(12) United States Patent
Mullaney

(10) Patent No.: US 10,299,832 B2
(45) Date of Patent: May 28, 2019

(54) EXTERNAL BONE FIXATION SYSTEMS

(71) Applicant: AMDT Holdings, Inc., Collierville, TN (US)

(72) Inventor: Michael W. Mullaney, Naples, FL (US)

(73) Assignee: AMDT Holdings, Inc., Collierville, TN (US)

( * ) Notice: Subject to any disclaimer, the term of this patent is extended or adjusted under 35 U.S.C. 154(b) by 0 days.

(21) Appl. No.: 15/977,694

(22) Filed: May 11, 2018

(65) Prior Publication Data

US 2018/0256210 A1 Sep. 13, 2018

Related U.S. Application Data

(63) Continuation of application No. PCT/US2017/020285, filed on Mar. 1, 2017.

(60) Provisional application No. 62/301,768, filed on Mar. 1, 2016.

(51) Int. Cl.
*A61B 17/64* (2006.01)
*A61B 17/56* (2006.01)
*A61B 17/68* (2006.01)
*A61B 17/88* (2006.01)
(Continued)

(52) U.S. Cl.
CPC .......... *A61B 17/6475* (2013.01); *A61B 17/56* (2013.01); *A61B 17/64* (2013.01); *A61B 17/6416* (2013.01); *A61B 17/6458* (2013.01); *A61B 17/6483* (2013.01); *A61B 17/68* (2013.01); *A61B 17/88* (2013.01);
(Continued)

(58) Field of Classification Search
CPC ..... A61B 17/64; A61B 17/66; A61B 17/6416; A61B 17/6425; A61B 17/645; A61B 17/6458; A61B 17/6466; A61B 17/6475; A61B 17/6483
USPC .................................................... 606/54–59
See application file for complete search history.

(56) References Cited

U.S. PATENT DOCUMENTS

| 5,601,551 A | 2/1997 | Taylor et al. |
| 9,872,706 B1 | 1/2018 | Mullaney et al. |
| 2005/0251135 A1 | 11/2005 | Riccione et al. |

(Continued)

OTHER PUBLICATIONS

International Search Report and Written Opinion issued in PCT/US2017/020285, dated May 25, 2017.

*Primary Examiner* — Julianna N Harvey
*Assistant Examiner* — Christina Negrellirodriguez
(74) *Attorney, Agent, or Firm* — Heslin Rothenberg Farley & Mesiti P.C.

(57) ABSTRACT

The present application provides external bone and tissue fixation systems and related methods. The fixation systems may include an elongate beam element defining an axis with an axially extending threaded track portion. The systems may also include at least one drivable fixation clamp assembly comprising a housing with a central bore, a driving housing rotatably coupled to the housing, a threaded driving member, and a clamp assembly rotatably coupled to the housing configured to clamp to at least one fixation member. The elongate beam element may extend axially through central bore of the housing. The driving member may be movable with respect to the central bore via rotation of the driving housing between engaged and disengaged states with the threaded track portion. Rotation of the driving member in the engaged state may axially translate the clamp assembly along the beam element.

45 Claims, 39 Drawing Sheets

(51) Int. Cl.
    *A61B 17/66* (2006.01)
    *A61B 17/86* (2006.01)
(52) U.S. Cl.
    CPC ........... *A61B 17/6425* (2013.01); *A61B 17/66* (2013.01); *A61B 17/8605* (2013.01)

(56) References Cited

U.S. PATENT DOCUMENTS

| | | | |
|---|---|---|---|
| 2010/0100096 A1* | 4/2010 | Hollawell | A61B 17/6416 606/59 |
| 2012/0095462 A1* | 4/2012 | Miller | A61B 17/6466 606/59 |
| 2015/0250501 A1 | 9/2015 | Orsak et al. | |

\* cited by examiner

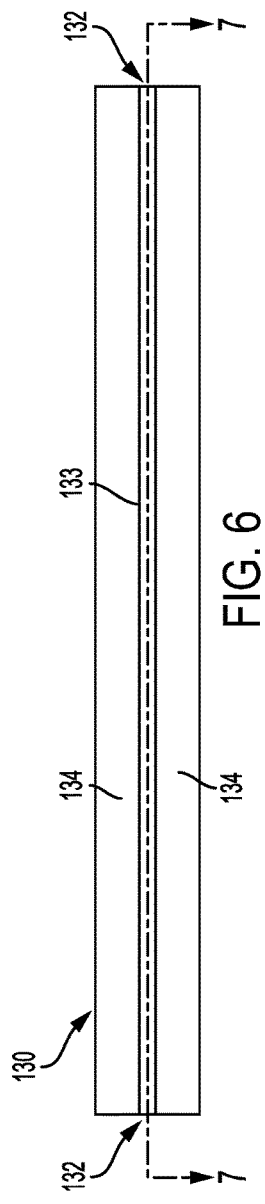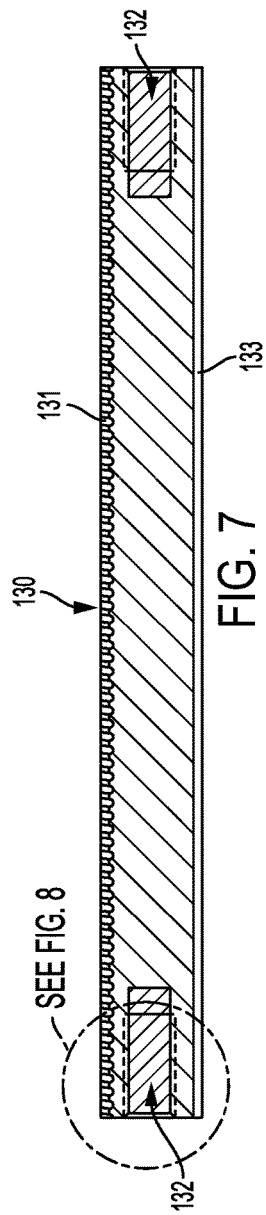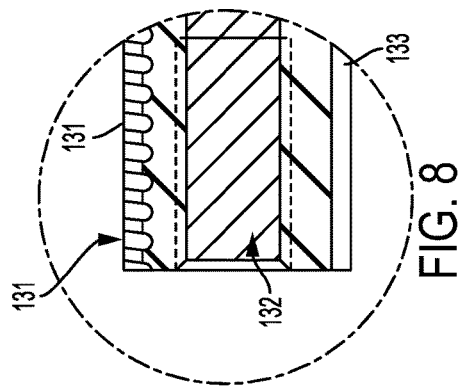

EXTERNAL BONE FIXATION SYSTEMS

CROSS-REFERENCE TO RELATED APPLICATIONS

The present application is a continuation of International PCT Patent Application No. PCT/US2017/020285, filed Mar. 1, 2017 and entitled External Bone Fixation Systems, which claims the benefit of U.S. Provisional Patent Application No. 62/301,768, filed Mar. 1, 2016 and entitled Mini External Bone Fixation Systems, the contents of which are hereby expressly incorporated herein by reference in their entirety.

FIELD OF THE INVENTION

The present disclosure is generally directed to external bone fixation systems and related methods. More particularly, the present disclosure is directed to external bone fixation systems and related methods that include a plurality drivable clamp elements arranged longitudinally along a beam element.

BACKGROUND OF THE INVENTION

External fixation devices have been used to treat bone and tissue conditions by positioning bone or tissue segments in desired relative positions based on particular clinical needs. One form of external fixation devices is a unilateral or mono-lateral rail based fixation device. These devices are typically comprised of a beam element serving as the structural backbone of the device, along which are slidably attached clamp assemblies that can accept fixation elements such as bone fixation pins or wires. In some embodiments, these clamp assemblies have the ability to be statically locked to the beam element or dynamically driven or translated axially along the beam element. In some embodiments, the clamp assemblies can be rotated about the beam element or angulated relative to the axis of the beam element.

When configured as bone or tissue fixation systems, unilateral fixation systems typically include a multitude of clamp assemblies. In the most basic configurations, there is one static clamp assembly and one drivable clamp assembly coupled to the beam element. In some embodiments, the beam element and the clamp assemblies arranged in this way can be connected to a second beam and clamp assembly through the use of a joint element having 1 or more degrees of freedom, such as a hinge having 1 degree of freedom to a spherical or cardan joint having 3 degrees of freedom. In more complicated configurations, it is sometimes desirable to be able to drive multiple clamp assemblies independently along the beam element such that multiple bone segments can be manipulated thereby. When affixing clamp assemblies to the fixation elements coupled to corresponding bone segments, it is also at times desirable to be able to quickly arrange the clamp assemblies along the beam element. Current unilateral external bone fixation systems do not aloe for such gross and/or quick translation of the clamp assemblies along the beam element, at least without adding or removing parts of the clamp assemblies and/or beam element. Given the small size of many unilateral external bone fixation systems utilized with relatively small bones (e.g., bones of the foot, hand or the like), adding or removing parts of the clamp assemblies and/or beam element can be cumbersome and/or time consuming.

External bone fixation systems with compact, clutch-able, self-contained mechanisms that allows for the rapid buildup and placement of clamp assemblies along the length of a beam element in a variety of positions and angulations to facilitate optimal fixation to bone elements (and thereby corresponding bones or bone segments) is therefore desirable.

SUMMARY OF THE INVENTION

In one aspect, the present disclosure provides external fixation systems (such as relatively small external fixation systems configured for use with relatively small bones), comprised of a longitudinal beam element that accepts and guides a multitude of clamp assemblies (potentially of differing configurations) positionable in differing orientations relative to the beam element. The beam element may include an axial engagement feature along the length of the beam element that serves as a point of engagement for each of the clamp assemblies, which is configured to allow the clamp assemblies to be locked in place along the length of the beam element and to be selectively driven or translated along the beam element. In another aspect of the present disclosure, an engageable feature of the clamp assemblies that is configured to selectively engage with or run free of the axial engagement feature of the beam element is provided. Means of effectuating engagement and disengagement of the engageable feature of the clamp assemblies and the axial engagement feature of the beam element is also provided.

In another aspect, a means of driving each of the clamp assemblies along the beam element through the use of an instrument that is not interfered with by the proximity of a clamp assembly relative to an adjacent clamp assembly is provided. In some embodiments, the clamp assemblies (and potentially the driving instrument) may be configured to allow the driving instrument to pass through the drivable element within the clamp assemblies and drivably engage with only a drive element that lies at the end of the instrument. Such a configuration may allow for access along a common drivable axis from a non-obstructed end of the beam element, for example.

In another aspect, means of attaching a clamp assembly to an end of the beam element that allows rotation of fixation elements coupled thereto about an axis that is normal to the axis of the beam element, and rotation of the of fixation elements within a plane parallel with that axis, is provided.

In another aspect, the present disclosure provides an external bone or tissue fixation system comprising an elongate beam element and at least one drivable fixation clamp assembly. The elongate beam element defines an axis and comprises an axially extending threaded track portion. The at least one drivable fixation clamp assembly comprises a main housing with a central bore, a driving housing rotatably coupled within an opening of the main housing, a threaded driving member in communication with the driving housing, and a clamp assembly selectively rotatably coupled to the main housing configured to clamp to at least one fixation member. The elongate beam element extends axially through central bore of the main housing. The driving member is movable with respect to the central bore via rotation of the driving housing between an engaged state with the threaded track portion and a disengaged state from the threaded track portion. Rotation of the driving member in the engaged state axially translates the at least one drivable fixation clamp assembly along the beam element.

In some embodiments, the beam element includes an axially extending alignment groove, and the central bore of the least one drivable fixation clamp assembly includes an anti-rotation member that extends into the alignment groove to rotationally fix the least one drivable fixation clamp assembly and the beam element about the axis of the beam element. In some such embodiments, the at least one drivable fixation clamp assembly comprises a plurality of drivable fixation clamp assemblies axially positioned along the beam element. In some such embodiments, the alignment groove of the beam element and the anti-rotation members of the plurality of drivable fixation clamp assemblies position the plurality of drivable fixation clamp assemblies about the axis of the beam element such that the driving members are coaxial. In some other such embodiments, the driving members include a through aperture extending axially therethrough, and the through apertures of the plurality of drivable fixation clamp assemblies are fully positioned within the central bore of the respective main housing in the engaged state.

In some embodiments, the driving member includes a through aperture extending axially therethrough, and the through aperture of the driving member is fully positioned within the central bore of the main housing in the engaged state. In some such embodiments, the through aperture of the driving member is configured to mate with a driving portion of a driving tool to effectuate rotation of the driving member. In some such embodiments, the system further comprises the driving tool, and the driving tool comprises a proximate portion that is configured to pass through the through aperture of the driving member.

In some embodiments, the clamp assembly is selectively rotatable partially about the axis of the beam element. In some embodiments, the clamp assembly is selectively rotatable about an axis that extends perpendicular to the axis of the beam element.

In some embodiments, the clamp assembly comprises a bearing screw with a head portion positioned within a slot of the main housing. In some such embodiments, the slot of the main housing extends partially about the axis of the beam element. In some other such embodiments, the clamp assembly further comprises a saddle member in abutment with a first portion of the outer surface of the main housing. In some embodiments, the first portion of the outer surface of the main housing extends partially about the axis of the beam element. In some embodiments, the clamp assembly further comprises a clamp base member in abutment with the saddle member, and a clamp top member positioned on an opposing side the clamp base member than the saddle member, and the clamp assembly is configured to clamp to the at least one fixation member between the clamp top member and the clamp base member. In some such embodiments, mating surfaces of the clamp base member and the saddle member include a friction increasing profile.

In some other such embodiments, the bearing screw extends through the saddle member, the clamp base member and the clamp top member such that a threaded portion extends past the clamp top member, and the clamp assembly further comprises a nut threadably engaged with the threaded portion of the bearing screw. In some such embodiments, translation of the nut along the bearing screw towards the head portion effectuates a compressive force to the at least one fixation member when positioned between the clamp top member and the clamp base member. In some other such embodiments, translation of the nut along the bearing screw towards the head portion effectuates a compressive force to the main housing between the head portion of the bearing screw and the saddle member to rotationally fix the clamp assembly about the axis of the beam element. In some other embodiments, translation of the nut along the bearing screw towards the head portion effectuates a compressive force between the saddle member and the clamp base member to rotationally fix the clamp base member and the clamp top member about the bearing screw.

In some embodiments, the driving housing is rotationally fixed to the main housing in the engaged state via at least one movable pin that extends within the driving housing and the main housing and is offset from the axis of rotation of the driving housing. In some such embodiments, removal of the at least one movable pin from the driving housing or the main housing effectuates the disengaged state. In some embodiments, the driving housing is rotationally fixed with respect to the main housing in the engaged state via at least one set screw extending between the main housing and the driving housing. In some such embodiments, the at least one set screw is axially translatable within the main housing along a direction that is angled with respect to the axis of rotation of the driving housing. In some other such embodiments, the at least one set screw is axially translatable within the main housing along a direction that is perpendicular with respect to the axis of rotation of the driving housing. In some such embodiments, the at least one set screw is axially translatable between a first position that rotates the driving housing such that the driving member is moved at least partially into the central bore and into the engaged state, and a second position that allows the driving housing to rotate such that the driving member is moved at least partially out of the central bore and into the disengaged state.

In some embodiments, the system further comprises at least one end fixation clamp assembly fixed to an axial end of the beam element. In some such embodiments, the at least one end fixation clamp assembly is axially fixed to the axial end of the beam element. In some other such embodiments, the at least one end fixation clamp assembly comprises a second main housing with a second central bore, and a second clamp assembly selectively rotatably coupled to the second main housing configured to clamp to at least one second fixation member. In some such embodiments, the at least one end fixation clamp assembly is fixed to the axial end of the beam element via a cap screw extending through the second main housing and threadably engaged within an internally threaded aperture extending axially within the beam element from the axial end thereof. In some other such embodiments, the at least one end fixation clamp assembly is rotationally fixed to the beam element about the axis of the beam element via at least one pin that extends within the second main housing and within an axially extending alignment groove of the beam element.

In some other such embodiments, the second clamp assembly further comprises a second bearing screw with a second head portion positioned within a second slot of the second main housing. In some such embodiments, the second slot of the second main housing extends about an axis of the central bore of the second main housing that is perpendicular to the axis of the beam element.

In some other such embodiments, the second clamp assembly further comprises a second saddle member in abutment with a second portion of the outer surface of the second main housing. In some such embodiments, the second portion of the outer surface of the second main housing extends partially about an axis of the central bore of the second main housing that is perpendicular to the axis of the beam element. In some other such embodiments, the second clamp assembly further comprises a second clamp base member in abutment with the second saddle member, and a second clamp top member positioned on an opposing side the second clamp base member than the second saddle member, and the second clamp assembly is configured to clamp to the at least one second fixation member between the second clamp top member and the second clamp base member. In some such embodiments, mating surfaces of the clamp base member and the saddle member include a friction increasing profile.

In some embodiments, the second bearing screw extends through the second saddle member, the second clamp base member and the second clamp top member such that a threaded portion extends past the second clamp top member, and wherein the second clamp assembly further comprises a second nut threadably engaged with the threaded portion of the second bearing screw. In some such embodiments, translation of the second nut along the second bearing screw towards the head portion effectuates a compressive force to the at least one second fixation member when positioned between the second clamp top member and the second clamp base member. In some other such embodiments, translation of the second nut along the second bearing screw towards the head portion effectuates a compressive force to the second main housing between the head portion of the second bearing screw and the second saddle member to rotationally fix the second clamp assembly about the axis of the central bore. In some other such embodiments, translation of the second nut along the second bearing screw towards the head portion effectuates a compressive force between the second saddle member and the second clamp base member to rotationally fix the second clamp base member and the second clamp top member about the second bearing screw.

In some embodiments, the system further comprises a clamp guide positioned within the central bore of the second main housing, the clamp guide including a narrowing internally threaded aperture. In some such embodiments, the system further comprises a clamp screw including a through aperture and an axially extending slot, the clamp screw being configured to threadably engage within the narrowing internally threaded aperture of the clamp guide. In some such embodiments, the through aperture of the clamp screw is configured to accept a third fixation member therethrough, and translation of the clamp screw within the narrowing aperture of the clamp guide effectuates a compressive force to the through aperture of the clamp screw to fix a third fixation member positioned therein to the at least one end fixation clamp assembly.

These and other objects, features and advantages of this disclosure will become apparent from the following detailed description of the various aspects of the disclosure taken in conjunction with the accompanying drawings.

BRIEF DESCRIPTION OF THE DRAWINGS

For the purposes of illustrating the external bone and/or tissue fixation systems and related fixation methods described herein, illustrative embodiments are provided. These illustrative embodiments are in no way limiting in terms of the precise configuration, arrangement and operation of the disclosed external bone and/or tissue fixation systems, and other similar embodiments are envisioned.

FIG. 6 is a side view of the beam element of FIG. 4.

FIG. 7 is a cross-sectional view of the beam element of FIG. 4 as indicated in FIG. 6.

FIG. 8 is an enlarged cross-sectional view of a portion of the beam element of FIG. 4 as indicated in FIG. 7.

DETAILED DESCRIPTION

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Any examples of parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein.

Figure 1:
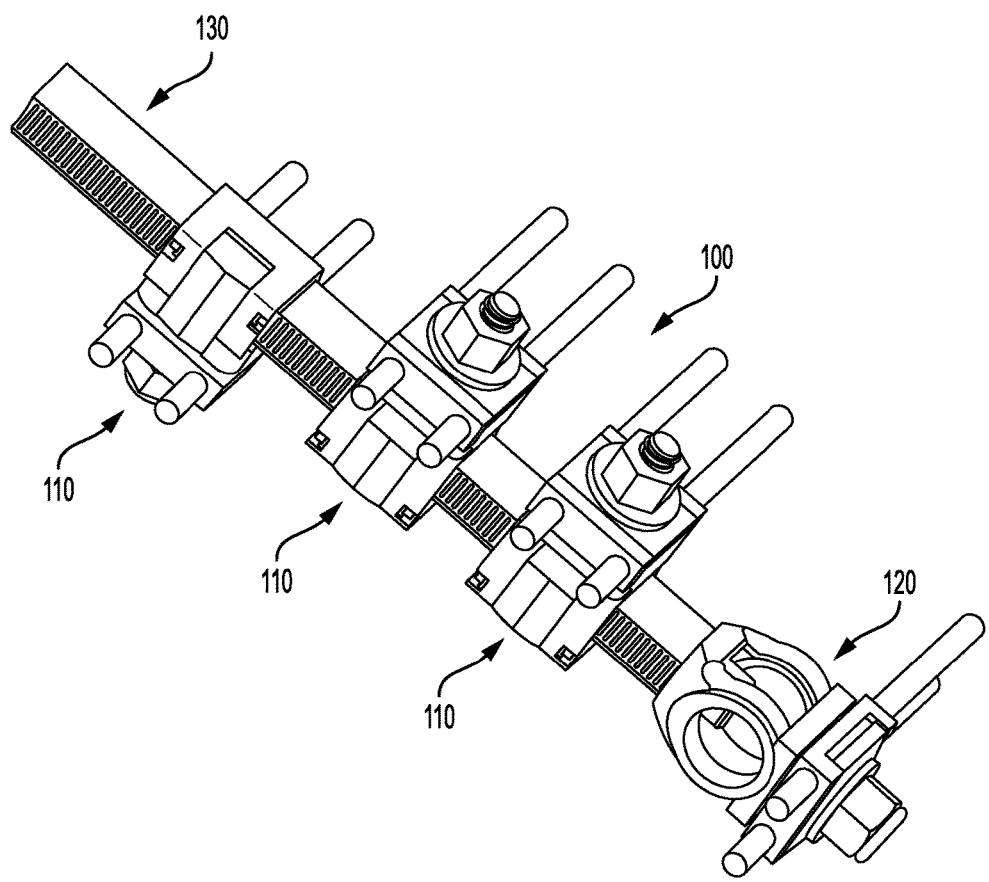
FIG. 1 is a perspective view of an external fixation system including a plurality of clamp assemblies arranged in an orthogonal fashion along an axis of a beam element.
Figure 2:
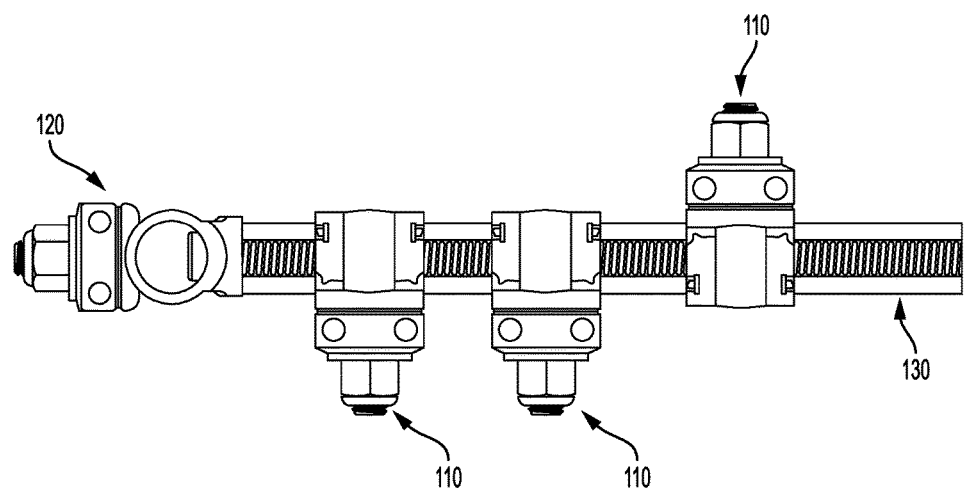
FIG. 2 is a side view of the external fixation system of FIG. 1.
Figure 3:
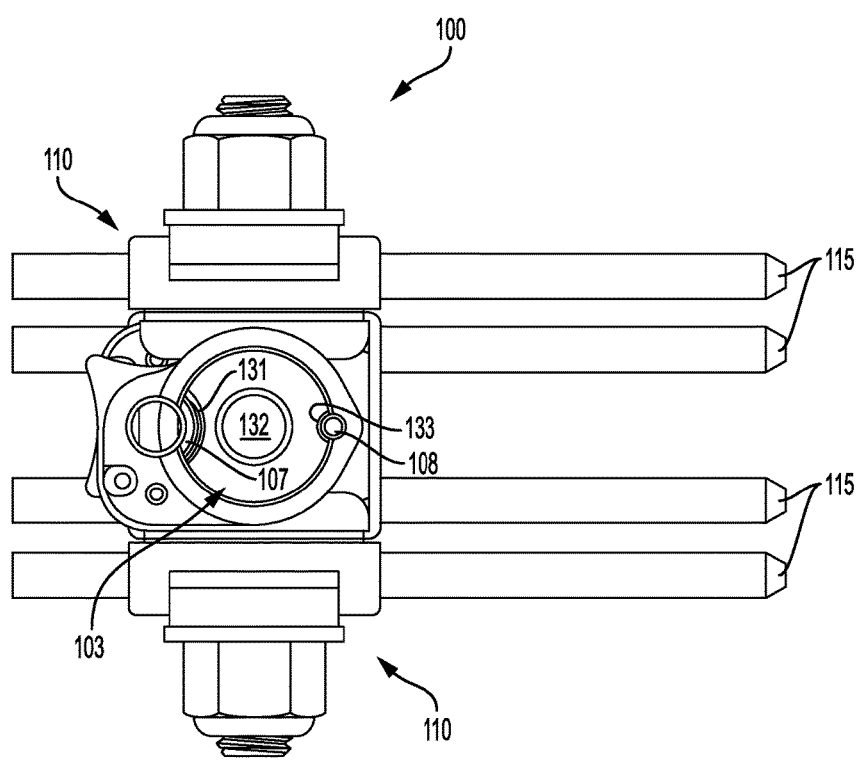
FIG. 3 is a top or end view of the external fixation system of FIG. 1.
Figure 4:
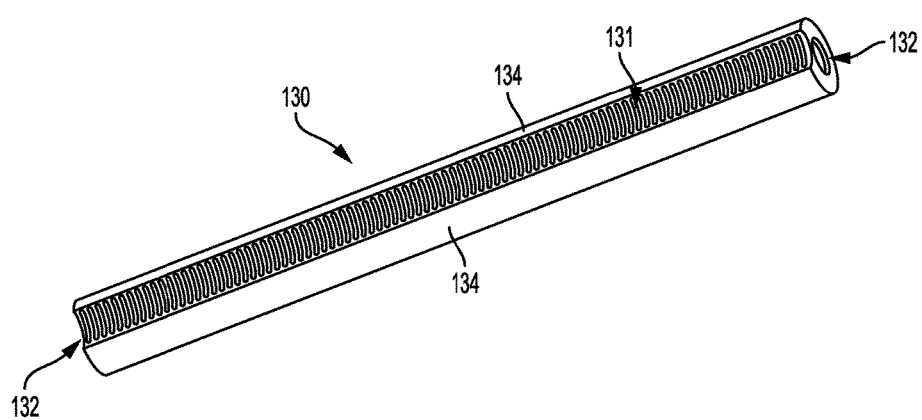
FIG. 4 is a perspective view of the beam element of the external fixation system of FIG. 1.
Figure 5:
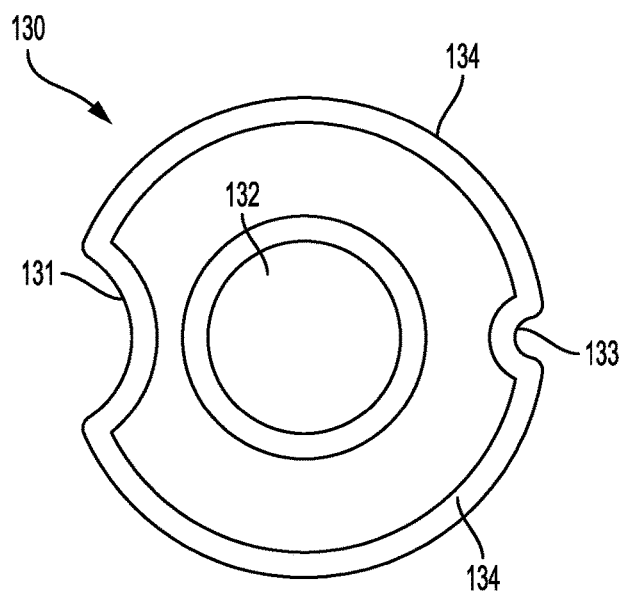
FIG. 5 is a top or end view of the beam element of FIG. 4.
Figure 9:
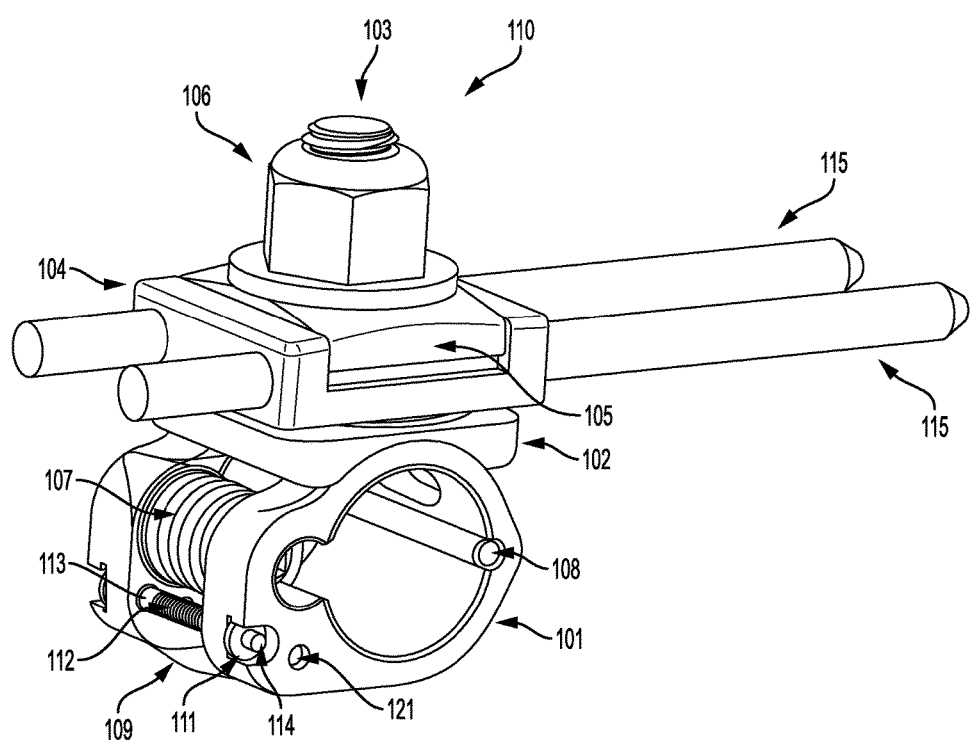
FIG. 9 is a perspective view of a drivable clamp assembly of the external fixation system of FIG. 1 coupling a pair of bone fixation members in a parallel arrangement.
Figure 10:
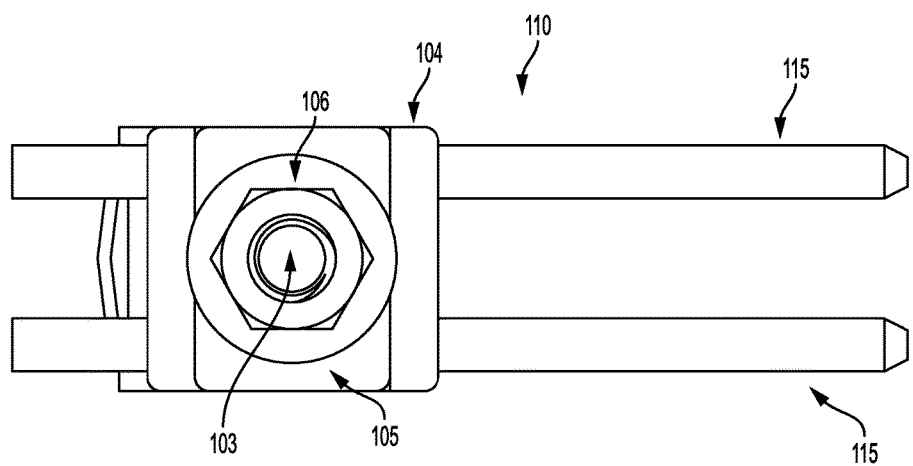
FIG. 10 is a top view of the drivable clamp assembly of FIG. 9.
Figure 11:
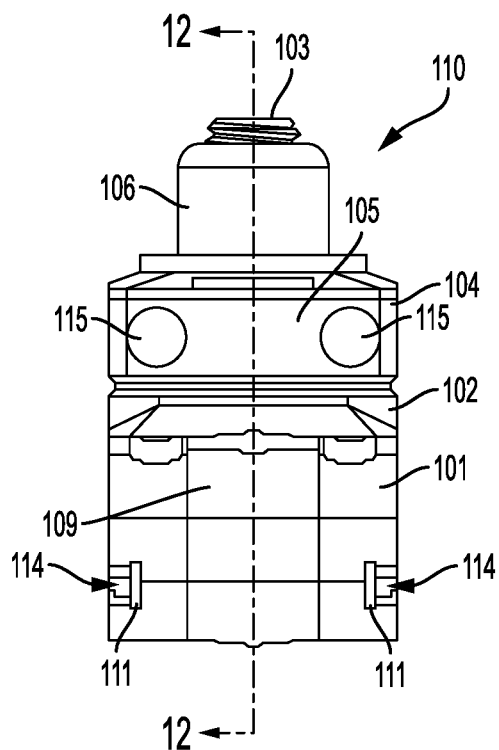
FIG. 11 is a side view of the drivable clamp assembly of FIG. 9.

The present disclosure provides for five degrees of freedom (5DOF) external bone or tissue fixation systems and related fixation methods 100, as shown in FIGS. 1-3, which are stable and mobile constructs. The fixation systems and methods 100 include one or more independently drivable clamp assemblies 110 (which may provide at least 3DOF) that are translatable or drivable along a beam element 130, and at least one fixed rotatable end clamp assembly 120 (which may provide at least 2DOF) positioned at an end of the beam element 130, as shown in FIGS. 1-3. The fixation systems and methods 100 of FIGS. 1-3 may be configured or particularly advantageous for use with relatively small bones, such as bones of the hand or foot. For example, the fixation systems and methods 100 of FIGS. 1-3 may be configured or particularly advantageous to fix two or more bones or bone segments of one or more relatively small bone with respect to each other, such one or more bones of the hand or foot. In some embodiments, the fixation systems and related fixation methods 100, as shown in FIGS. 1-3, may be configured or particularly advantageous for the repair of fractures or deformities of one or more bone, such as fractures of or deformities in one or more relatively small elongate bone in a hand or foot. In some embodiments, the fixation systems and related fixation methods 100

The present application provides external bone fixation systems for long bones of the hands and feet. The systems include mini rail systems that have the ability to have separately movable and drivable clamp assemblies 110 located along the length of the rail element 130 with provisions to allow for the attachment of non-traveling clamp assemblies 120 or additional rail elements 130 and traveling assemblies 110 through the use of a joint element, such as but not limited to a hinge or spherical joint.

As shown in FIGS. 1-3, the beam element 130 to which the at least one drivable clamp assemblies 110 and at least one end clamp assembly 120 are coupled may be an elongate element or beam 130 that defines an axis or linear length along a first direction. As shown in FIGS. 1-3, at least one rotatable end clamp assembly 120 may be removably coupled to an end of the beam element 130, and at least one drivable clamp assembly 110 may be translatably or drivably coupled to the exterior of the beam element 130, such as a plurality of drivable clamp assemblies 110 translatably coupled to the exterior of the beam element 130 spaced along the axis or axial length of the beam element 130. For example, FIGS. 1 and 2 illustrate the exemplary fixation systems and method 100 in a first configuration with the plurality of drivable clamp assemblies 110 arranged in an orthogonal fashion along the main axis of the beam element 130, with the rotatable end clamp assembly 120 coupled to an axial end of the beam element 130. As shown in FIG. 3, in the first configuration the plurality of drivable clamp assemblies 110 are arranged on opposing sides (e.g., anterior and posterior) along the main axis of the beam element 130, and are also shown in an orthogonal arrangement. As shown in FIGS. 1-3, in some embodiments the at least one drivable clamp assembly 110 may pass over the beam element 130. Stated differently, in some embodiments the beam element 130 may extend through the at least one drivable clamp assembly 110, and the at least one drivable clamp assembly 110 may be configured to translate along or over the exterior surface of the beam element 130.

As shown in FIGS. 4-8, the beam element 130 may be at least generally cylindrical and define an exterior surface that extends about the axis and between substantially opposing free ends (e.g., a generally cylindrical exterior surface with opposing bases or free ends). At least one end of the beam element 130 may include an aperture or hole 132 extending at least substantially axially into the beam element 130 from the end surface, as shown in FIGS. 4-8. The axially-extending aperture 132 may extend along the axial length of the beam element 130 at least partially into the interior or medial portion of the beam element 130 (along the axial direction). The at least one end aperture 132 of the beam element 130 may include internal threads such that the at least one end aperture 132 comprises a tapped hole 132. As shown in FIGS. 1-3, the at least one end aperture 132 may thereby be configured to threadably couple or mate with external threads of a bolt portion of a rotatable end clamp assembly 120 to removably couple the rotatable end clamp assembly 120 and the beam element 130. Similarly, the at least one end aperture 132 may thereby be configured to threadably couple or mate with external threads of another beam element 130 or connection mechanism (e.g., a dual threaded connection mechanism) to another beam element to removably couple the beam element 130 and the additional beam element. The beam element 130 may thereby be effectively axially lengthened via the additional beam element. In other embodiments, the beam element 130 and/or the at least one end aperture 132 of the beam element 130 may be non-threaded or include another configuration or mechanism besides internal threads for mating with a rotatable end clamp assembly 120 and/or an additional beam element.

As shown in FIGS. 4-8, the exterior surface of the beam element 130 may be generally cylindrical and include an externally threaded or patterned engagement track 131 and an alignment groove or slot 133. The externally threaded and/or the alignment groove 133 may extend along the axial length of the exterior surface of the beam element 130 for the entire length of the beam element 130 or partially along the length of the beam element 130. As shown in FIGS. 4-8, the engagement track 131 may be indented or recessed into the beam element 130. In this way, the track 131 may form a groove extending radially into or within the beam element 130. The engagement track 131 may form a portion of the exterior surface of the beam element 130. In some embodiments, as shown in FIGS. 4-8, the engagement track 131 may be a groove defined by a radius. As shown in FIGS. 4-8, the track 131 may include external threads (or internal threads, depending upon perspective) extending along the axial length of the track 131. As explained further below, the threads of the engagement track 131 may mate with threads of a driving member of a drivable clamp assembly 110 to allow the drivable clamp assembly 110 to be axially translated or driven along the length of the beam element 130 via the driving member. As such, the pitch of the threads of the engagement track 131 and the threads of the driving member of a drivable clamp assembly 110 may have compatible pitches and/or other configurations. In some embodiments, the engagement track 131 may be a hemispherical threaded groove extending into the beam element 130. It is noted that such a radial or hemispherical grooved threaded engagement track 131 may be machined relatively easily. For example, the hemispherical grooved threaded engagement track 131 may be machined via ball end-mill which alleviates difficulties associated with tap a relatively long partial bore, such as opposed to a standard 60 thread or a trapezoidal thread for example.

As also shown in FIGS. 4-8, similar to the engagement track 131, the alignment groove 133 may be indented or recessed into the beam element 130. In this way, the alignment groove 133 may form a groove extending radially into or within the beam element 130. The alignment groove 133 may form a portion of the exterior surface of the beam element 130. In some embodiments, as shown in FIGS. 4-8, the alignment groove 133 may be defined by a radius, such as a hemispherical groove. In other embodiments, the alignment groove 133 may be any other shape or configuration. The alignment groove 133 may couple with an alignment member (such as a pin or ball bearing) of a drivable clamp assembly 110 to allow the drivable clamp assembly 110 to be axially translated or driven along the length of the beam element 130 (via the driving member and engagement track 131) while being aligned or positioned in a particular orientation with the beam element 130, as explained further below. The alignment groove 133 may thereby serve as a linear, partially cylindrical groove that serves to provide anti-rotation of a drivable clamp assembly 110 about the beam element 130, as explained further below. The alignment groove 133 and the drivable clamp assembly 110 may mate via the alignment member only in a particular relative orientation between the drivable clamp assembly 110 and the beam element 130, and may prevent the drivable clamp assembly 110 from rotating about the beam element 130 from such an orientation (but allow the drivable clamp assembly 110 to translate or slide axially along the alignment groove 133 when being axially driven via the driving member thereof.

In some embodiments, the beam element 130 may include intermediate exterior surface portions 134 extending between the alignment groove 133 and the engagement track 131 portions of the beam element 130, as shown in FIGS. 4-8. In some embodiments, the alignment groove 133 and the engagement track 131 portions of the beam element 130 may substantially oppose each other about the axis of the beam element 130, and thereby two substantially similar intermediate exterior surface portions 134 may extend therebetween. In other embodiments, the alignment groove 133 and the engagement track 131 portions of the beam element 130 may be offset about the axis of the beam element 131. As shown in FIGS. 4-8, the intermediate exterior surface portions 134 may be substantially smooth surfaces (e.g., non-threaded surfaces), and may be curved or arcuate. In some embodiments, the intermediate exterior surface portions 134 may be may be cylindrical surface portions extending about the axis of the beam element 130 (e.g., convex surfaces defined by a single radius) and/or along the axial length of the beam element 130.

Referring to FIGS. 9-19, the drivable or traveling clamp assemblies 110 may be configured to selectively translate along the axial length of the beam element 130 (and over the exterior surface of the beam element 130) and removable couple or fix to one or more fixation members 15. As shown in FIGS. 9-19, the drivable clamp assembly 110 may include a main housing 101 with a central bore extending therethrough that is configured to accept or allow the beam element 130 to extend axially therethrough. In this way, when the drivable clamp assembly 110 is coupled to the beam element 130, the axis of the central bore of the housing 101 and the axis of the housing 101 may be aligned. The interior surface of the central bore of the housing 101 may be configured to mate with the intermediate exterior surfaces 134 of the beam element 130 when the beam element 130 extends therethrough. In this way, the beam element 130 may be securely supported or held by the housing 101 to form a relatively stable construct. However, the interior surface of the central bore of the housing 101 and the intermediate exterior surfaces 134 of the beam element 130 may be configured to allow the drivable clamp assembly 110 to be slidably engaged about the beam element 130 through its main bore.

As shown in FIGS. 9, 12, 13, 16, 18 and 19, the central bore of the housing 101 may include a groove extending therethrough. As also shown in FIGS. 9, 12, 13, 16, 18 and 19, an anti-rotation member 108, such as a pin, may be positioned partially within the groove of the central bore of the housing 101 such that the anti-rotation member 108 extends into the central bore. In some embodiments, the anti-rotation member 108 may be pressed into the central bore of the housing 101 such that it is retained therein. By partially extending into the central bore of the housing 101, the anti-rotation member 108 may be seated or positioned within the alignment groove 133 of the beam element 130 when the beam element 130 extends through the central bore. In this way, the beam element 130 and the drivable clamp assemblies 110 may be orientated relative to each other such that the anti-rotation member 108 and the alignment groove 133 are aligned to extend the beam element 130 through the central bore of the housing 101 of the drivable clamp assemblies 110. Further, with the anti-rotation member 108 positioned within the housing 101 and the beam element 130 (and the housing 101 and the intermediate surface portions 134 of the beam element 130 maintaining alignment or concentricity thereof), the anti-rotation member 108 may prevent relative rotation of the drivable clamp assemblies 110 about the axis of the beam element 130 when the beam element 130 extends through the central bore of the housing 101. The anti-rotation member 108 being positioned within the housing 101 and the beam element 130 (and the housing 101 and the intermediate surface portions 134 of the beam element 130 abutting) may ensure the drive member 107 is aligned with, and is maintained in alignment with, the engagement track 131 of the beam element 130 when the beam element 130 extends through the central bore of the housing 101. In this way, the drive member 107 may be selectively engaged with the engagement track 131 when the when the beam element 130 extends through the central bore of the housing 101, as explained further below.

As shown in FIGS. 9 and 12-19, the drivable clamp assemblies 110 may include an externally threaded drive or driving member 107 configured to mate (e.g., threadably mate) with the engagement track 131 of the beam element 130 when the beam element 130 extends through the central bore of the housing 101 and the drive member 107 is in an engaged positioned, as explained further below. As noted above, the threads of the drive member 107 and the engagement track 131 may be compatible and configured to threadably engage. In some embodiments, the driving member 107 may be substantially cylindrical. As also shown in FIGS. 9 and 12-19, the drive member 107 may be contained or held within a partial bore of a release housing 109 of the drivable clamp assemblies 110. The drive member 107 may include a driving aperture extending therethrough, as shown in FIGS. 9 and 12-19. The driving aperture of the drive member 107 may be non-circular in cross-section or otherwise be configured such that it can be utilized to apply a torque or rotational force to the drive member 107. The axis of rotation or drive axis of the drive member 107 may be aligned with an axis of the driving aperture. The driving aperture of the drive member 107 may allow torque or rotational force to be applied to the drive member 107 (e.g., via a driving tool) to rotate the drive member 107 about its axis of rotation or drive axis. The driving aperture of the drive member 107 may be positioned within the central bore of the housing 101 of the drivable clamp assemblies 110 such that the driving aperture of the drive member 107 is accessible along the axis of the driving aperture. In some embodiments, the axis of rotation of the driving aperture and drive member 107 may be parallel to, but offset from, the axis of the beam element 130.

The release housing 109 of the drivable clamp assemblies 110 may be retained or restrained within an opening in the housing 101 through the use of at least one dowel pin 121 or other mechanism extending through the housing 101 that allows the release housing 109 to rotate within the opening of the housing 101, and thereby pivot into or out of the central bore of the housing 101, as also shown in FIGS. 9 and 12-19. The rotation of the release housing 109 within the opening of the housing 101, such as about the least one dowel pin 121, may be limited by the configuration of the housing 101 or otherwise limited. For example, rotation of the release housing 109 within the opening of the housing 101 may be limited by an interference with a slot face within the opening of the housing 101 in which it resides. Such limited rotation of the release housing 109 within the housing 101 may ensure that the drive screw 107 is retained within the housing 101.

Figure 17:
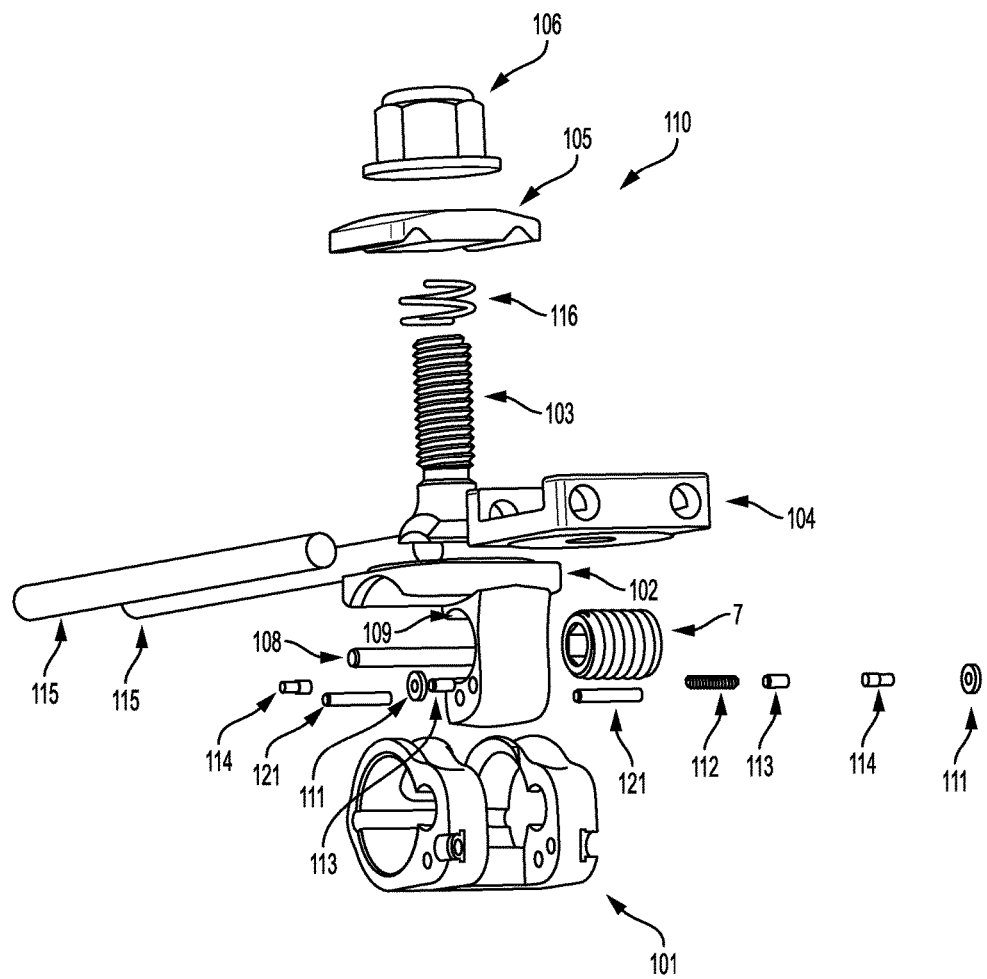
FIG. 17 is a perspective exploded view of a drivable clamp assembly of the external fixation system of FIG. 1.
Figure 18:
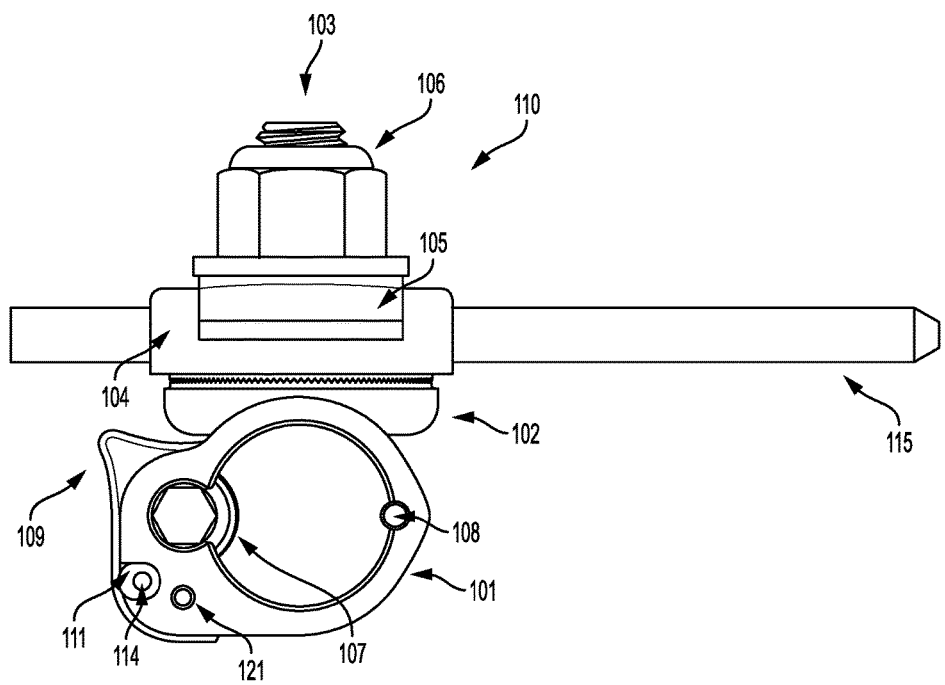
FIG. 18 is a side view of a drivable clamp assembly of the external fixation system of FIG. 1 illustrating the driving mechanism in an engaged position.

As shown in FIGS. 9 and 11-19, the position of the release housing 109 within the housing 101 may be controlled by one or more control pins 114 and springs 112, for example. The at least one control pin 114 and spring 112 may reside with an offset bore of the release housing 109 and/or housing 101 that lies about or offset from the rotational axis of the axis of rotation of the release housing 109 (e.g., is offset from the dowel pin 121), as shown in FIGS. 9 and 11-19. The at least one spring 112 may reside within the offset bore within the release housing 108, may apply outward axial pressure to the at least one control pin 114 to position the at least one control pin 114 partially in the offset bore within the release housing 108 and partially in the offset bore within the housing 101, thus holding the release housing 101 in an engaged position with the driving member 107 positioned partially within the central bore and into contact or engagement with the engagement track 131 of the beam element 130 (i.e., an engaged state of the drivable clamp assemblies 110), as shown in FIG. 18. In the engaged state of the drivable clamp assemblies 110, the at least one control pin 114 may retain the release housing 101 and the driving member 107 in the engaged position by extending within both the offset bore of the release housing 109 and the housing 101. In the engagement position, rotation of the driving member 107 about its axis of rotation may thereby force the drivable clamp assembly 110 to translate along the axial length of the beam element 130 due to the threaded engagement of the driving member 107 and the engagement track 131 (and the driving member 107 being axially captured within the housing 101). The threaded engagement of the driving member 107 and the engagement track 131 may thereby allow for relatively fine adjustment of the drivable clamp assembly 110 axially along the beam element 130 via rotation of the driving member 107 about its axis of rotation. Further, the threaded engagement of the driving member 107 and the engagement track 131 in the engaged state or position may also fix the drivable clamp assembly 110 along the axis of the beam element 130 when the driving member 107 is not axially rotated about its axis of rotation.

Figure 19:
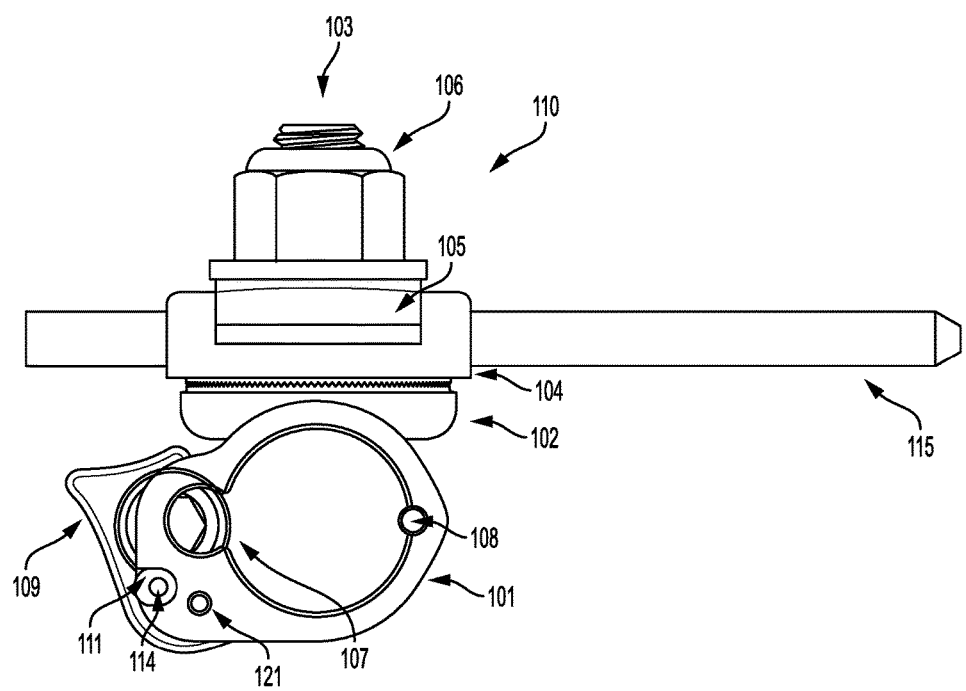
FIG. 19 is a side view of a drivable clamp assembly of the external fixation system of FIG. 1 illustrating the driving mechanism in a disengaged position.
Figure 20:
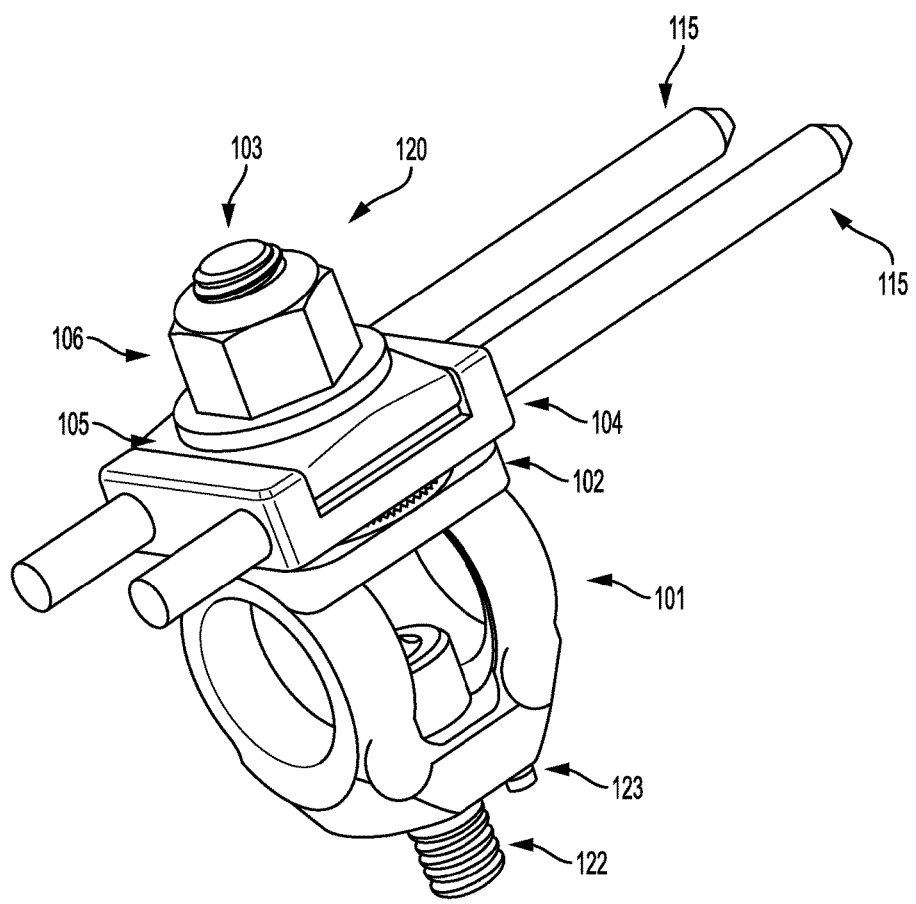
FIG. 20 is a perspective view of the end clamp assembly of the external fixation system of FIG. 1.
Figure 21:
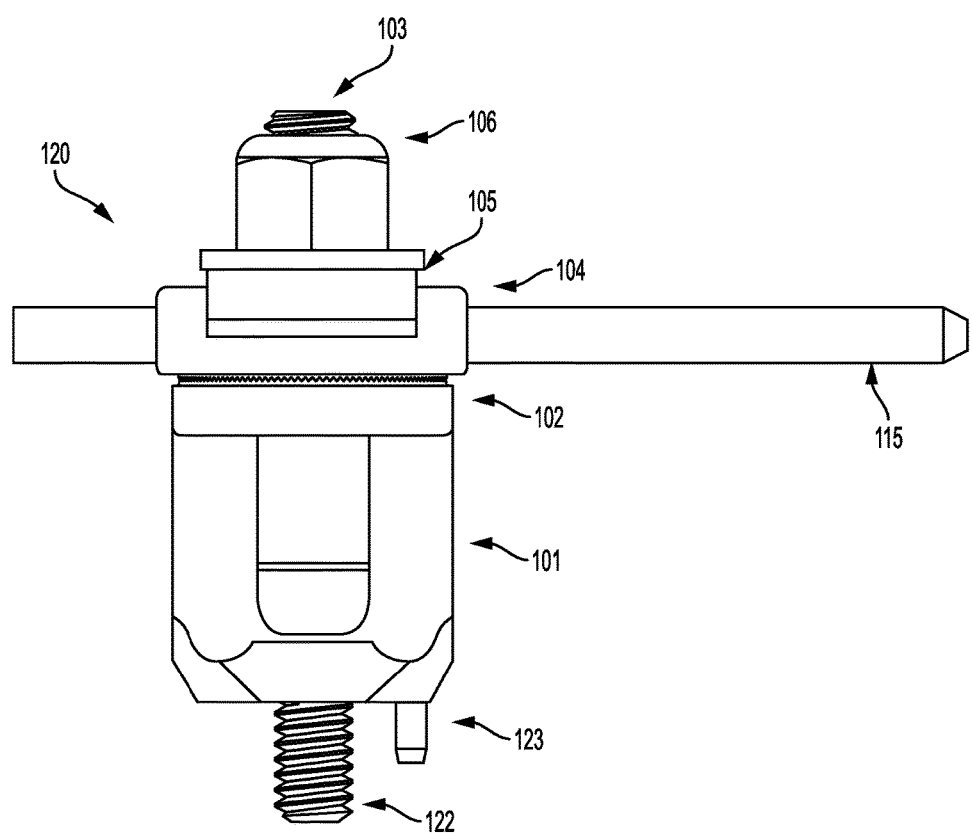
FIG. 21 is a side view of the end clamp assembly of FIG. 20.
Figure 22:
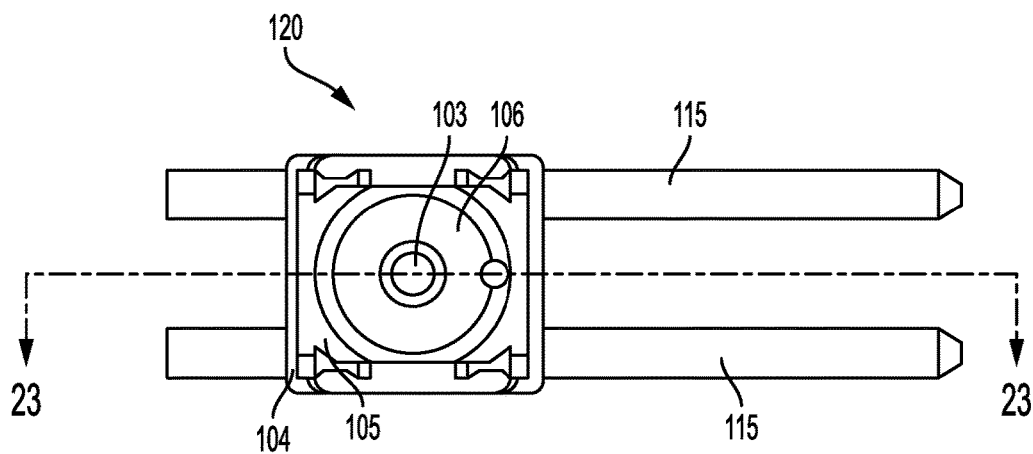
FIG. 22 is a top view of the end clamp assembly of FIG. 20.
Figure 23:
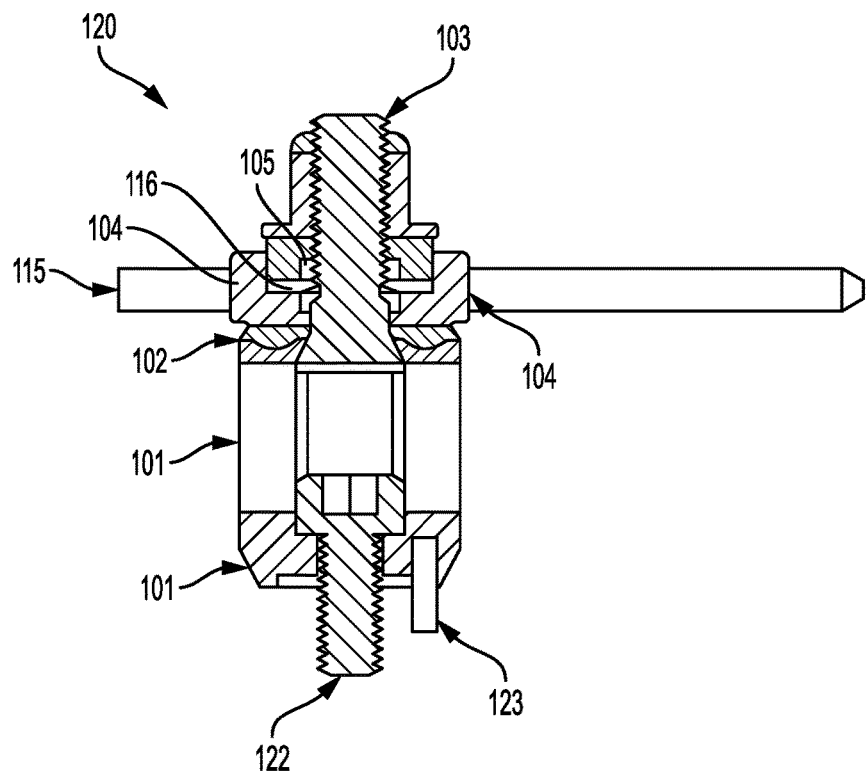
FIG. 23 is a cross-sectional view of the end clamp assembly of FIG. 20 as indicated in FIG. 22.
Figure 24:
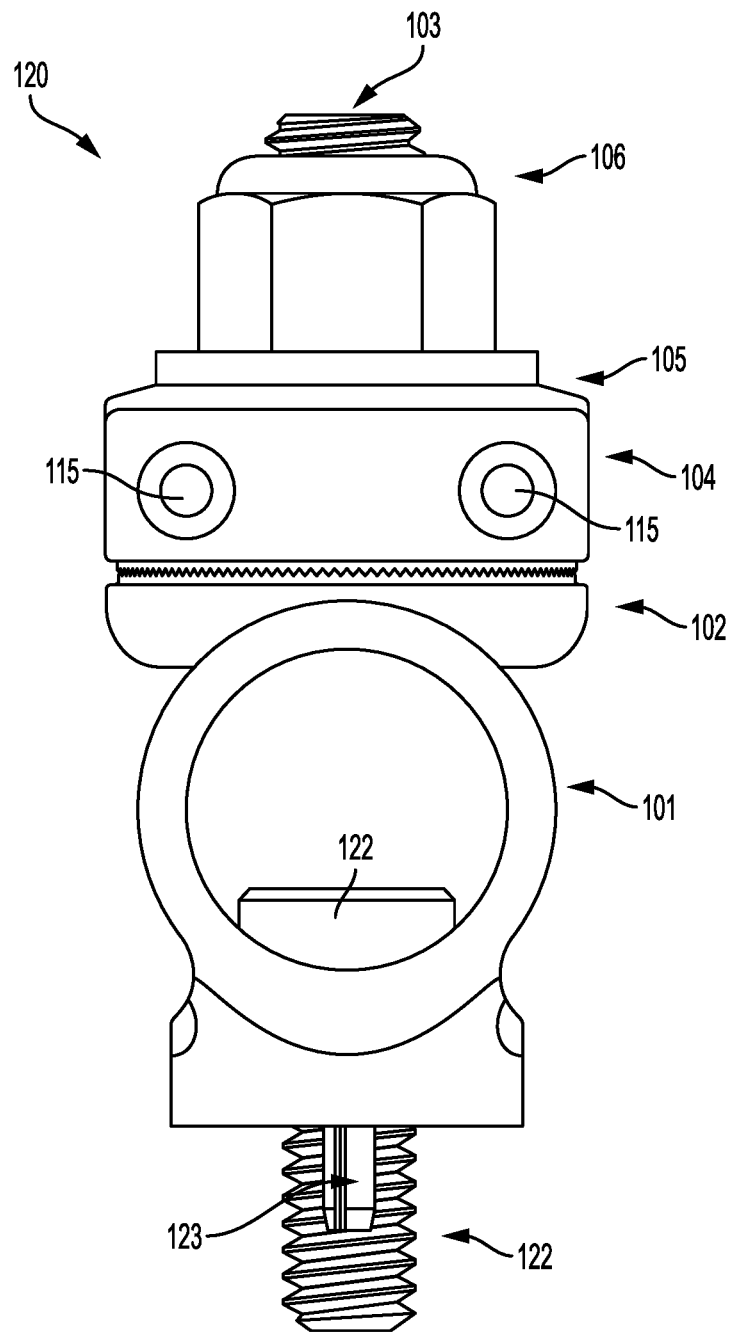
FIG. 24 is an axial side view of the end clamp assembly of FIG. 20.
Figure 25:
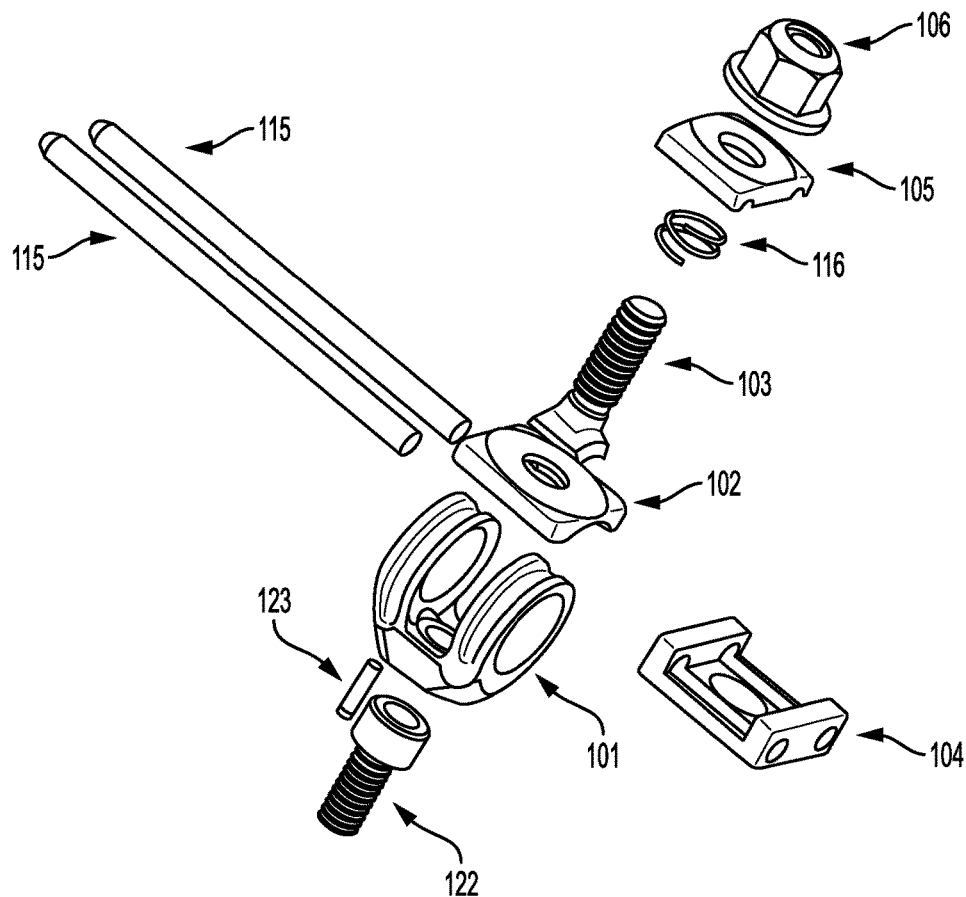
FIG. 25 is a perspective exploded view of the end clamp assembly of FIG. 20.

The drivable clamp assemblies 110 may be configured to be selectively moved from the engaged state to a disengaged state with the with the driving member 107 at least partially removed from within the central bore and out of contact or engagement with the engagement track 131 of the beam element 130 (i.e., a disengaged state of the drivable clamp assemblies 110). The disengaged state of the drivable clamp assemblies 110 may be effectuated by moving the at least one control pin 114 out of the offset bore of the housing 101, such as to fully within the release housing 109. As shown in FIGS. 9 and 11-19, in some embodiments the drivable clamp assemblies 110 may include at least one release pin 14 extending within the offset bore of the housing 101. The at least one release pin 14 may be retained within the offset bore of the housing 101 by virtue of a step of the at least one release pin 114 (e.g., between thicker and thinner portions) and at least one corresponding retention member or washer 111 that is positioned within a slot or undercut in the housing 101, as shown in FIGS. 9 and 11-19. The at least one release pin 114 may be configured such that when the at least one release pin 114 is translated further (e.g., completely) within the offset bore of the housing 101, such as via a tool, the at least one release pin 114 act against the at least one control pin 114 to push or translate the at least one control pin 114 out of the offset bore of the housing 101 (such as fully into the offset bar of the release housing 109). With the at least one control pin 114 removed from the offset bore of the housing 101, the release housing 109 is able to freely rotate about its axis of rotation, such as about the at least one pin 121. As such, with the at least one control pin 114 removed from the offset bore of the housing 101, the release housing 109 is able to rotate at least partially out from the central bore of the housing 101, and thereby allow the driving member 107 to also translate within the central bore of the housing 101 and out of engagement with the engagement track 131 of the beam element 130), as shown in FIG. 19. When the driving member 107 and the engagement track 131 are spaced or out of engagement (e.g., out of threaded engagement), the drivable clamp assembly 110 is free to axially translate along the beam element 130 without limitation, thereby allowing for gross adjustment of the drivable clamp assembly 110 axially along the beam element 130 and/or installation of the drivable clamp assembly 110 onto the beam element 130.

The engaged and disengaged states of the exemplary drivable clamp assembly 110 (and the release housing 109 and the driving member 107) is comparatively shown in FIGS. 18 and 19, respectively. As shown in FIG. 18, when in the engagement position or state, the driving aperture of the drive member 107 is positioned or aligned within the central bore of the housing 101 of the drivable clamp assemblies 110 such that the driving aperture of the drive member 107 is accessible along the axis of the driving aperture or the drive member 107.

As shown in FIGS. 9-13 and 15-19, the drivable clamp assemblies 110 may include a clamp assembly configured to removable couple to at least one bone fixation member 115 that is rotatable with respect to the housing 101 (and the central bore and a beam element 130 extending therethrough), such as an axis that is substantially perpendicular or normal to the axis of the central bore and/or a beam element 130 extending therethrough, and/or about the axis of the central bore and/or a beam element 130. As shown in FIGS. 9-13 and 15-19, the drivable clamp assemblies 110 may include a saddle 102 that is rotationally engaged to the housing 101 by an inner surface that engages an outer surface of the housing 101. For example, the inner surface of the housing may be concave, and the outer surface of the housing 101 may be convex (or vice-versa). The inner surface of the saddle 102 and the outer surface of the housing 101 may be configured such that the saddle 102 is able to slide over along the surface of the housing 101. In some embodiments, the inner surface of the saddle 102 and the outer surface of the housing 101 may be configured such that the saddle 102 is able to slide over along the surface of the housing 101 about the axis of the central bore and/or a beam element 130 extending therethrough. For example, the surface of the saddle 102 and the outer surface of the housing 101 may be cylindrical or arcuate surfaces defined by a radius extending from the axis of the central bore and/or a beam element 130 extending therethrough.

A top surface of the saddle 102, which may oppose the inner surface thereof, may include a substantially planar surface with a surface roughness or profile configured to provide friction between the top surface of the saddle 102 and a bottom surface of a clamp base member 104 that is configured to mate therewith, as shown in FIGS. 17-19. For example, the top surface of the saddle 102 and the bottom surface of a clamp base member 104 may include a poker chip style serration that emanates radially from a binding aperture or hole extending therethrough from the top surface to the bottom surface. However, any other surface texture configuration, or no surface texture (e.g., flat surfaces), may be utilized.

Figure 12:
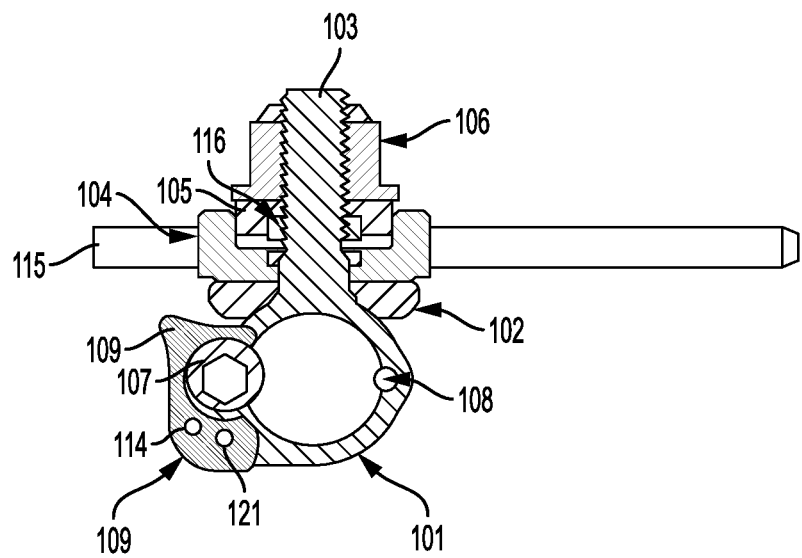
FIG. 12 is a cross-sectional view of the drivable clamp assembly of FIG. 9 as indicated in FIG. 11.
Figure 13:
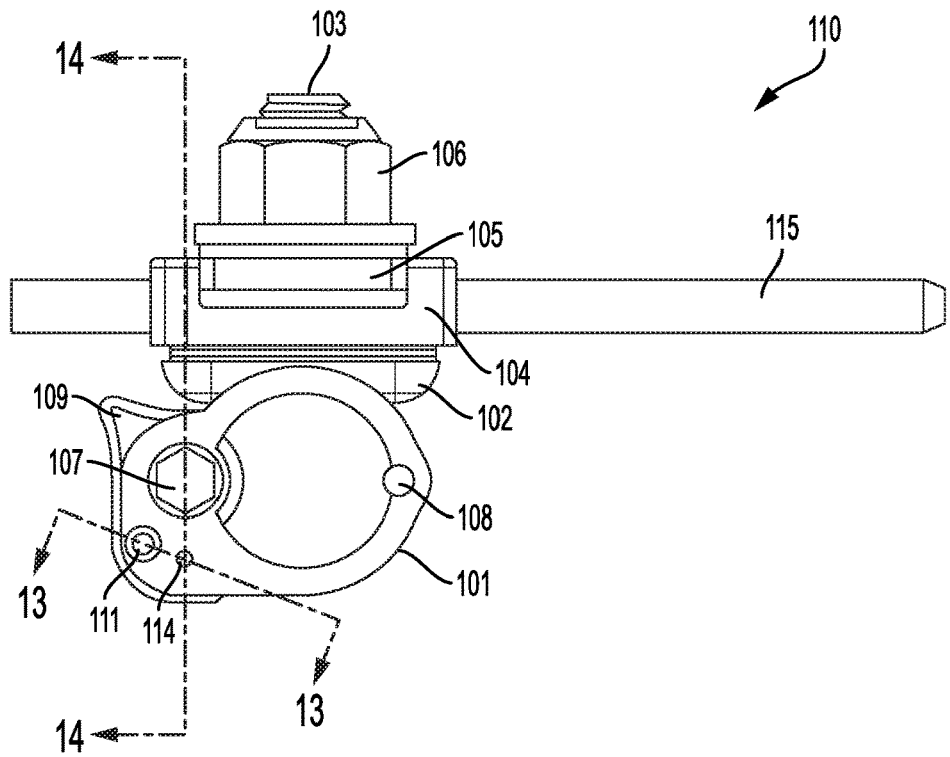
FIG. 13 is another side view of the drivable clamp assembly of FIG. 9.
Figure 14:
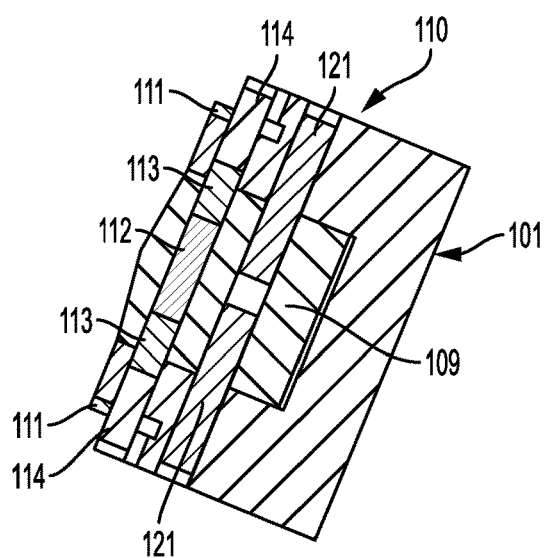
FIG. 14 is a cross-sectional view of the drivable clamp assembly of FIG. 9 as indicated in FIG. 13.
Figure 15:
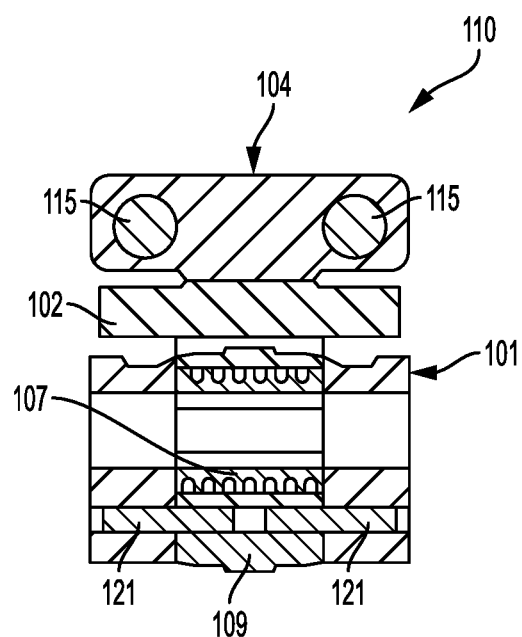
FIG. 15 is another cross-sectional view of the drivable clamp assembly of FIG. 9 as indicated in FIG. 13.
Figure 16:
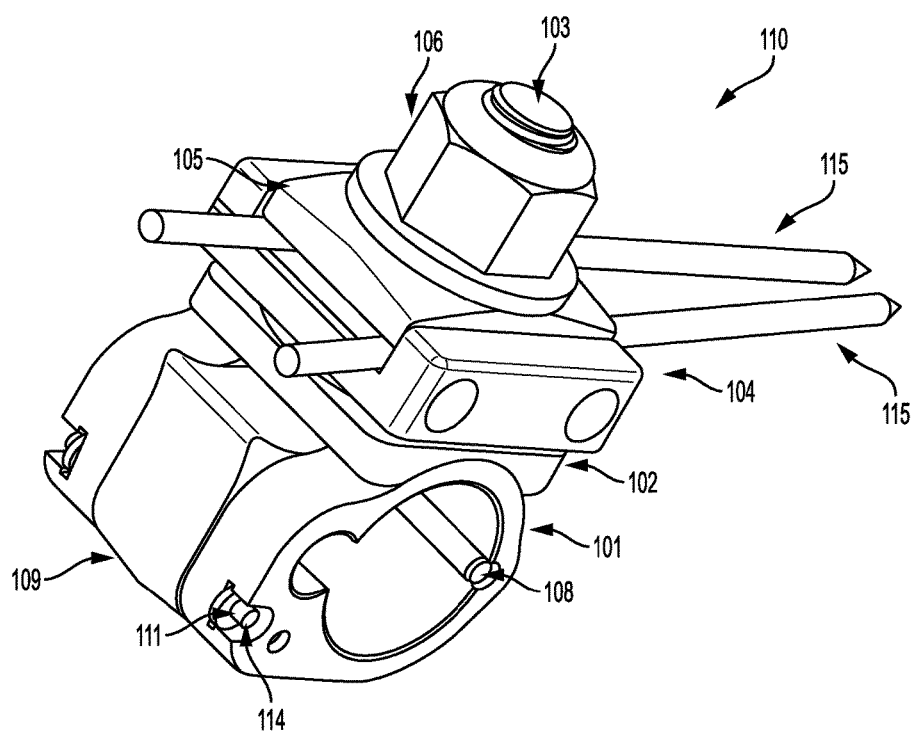
FIG. 16 is a perspective view of a drivable clamp assembly of the external fixation system of FIG. 1 coupling a pair of bone fixation members in a converging arrangement.

The binding aperture of the saddle 102 and the binding aperture of the clamp base member 104 may be configured to allow a binding screw 103 to extend therethrough and align the saddle 102 and the binding screw 103 to the axis of the binding screw 103, as shown in FIGS. 9-19. The binding screw 103 may include a head portion that is configured to be positioned within an upper slot of the housing 101 of the drivable clamp assemblies 110. The upper slot of the housing 101 of the drivable clamp assemblies 110 may be configured to prevent the binding screw 103 from translating out from the upper slot of the housing 101 in a direction extending along the axis of the binding screw 103 away from the central bore of the housing 101. For example, the inner edges or surfaces of the upper slot of the housing 101 may converge inwardly to a dimension smaller than the largest dimension of the head potion of the binding screw 103 away, as shown in FIGS. 12 and 17. However, the upper slot of the housing 101 may extend about the central bore of the housing 101 to allow the binding screw 103 to slide over along the upper slot of the housing 101 (e.g., inner edges or surfaces thereof) about the axis of the central bore and/or a beam element 130 extending therethrough, as shown in FIG. 17. For example, the inner edges or surfaces of the upper slot of the housing 101 may extend partially about the axis of the central bore and/or a beam element 130 extending therethrough, as shown in FIG. 17. In some embodiments, the upper slot of the housing 101 that houses the head portion of the binding screw 103 may be a tapered partial radial slot within the housing 101, which may or may not be machined integral with the housing 101. The outer surface of the binding screw 103 may be a mirror image of the inner edges or surfaces of the upper slot of the housing 101, or otherwise be configured, to prevent the binding screw 103 from disconnecting from the housing 101 in a direction extending along the axis of the binding screw 103 and to allow the binding screw 103 to translate at least partially about the axis of the central bore and/or a beam element 130 extending therethrough, as shown in FIGS. 12 and 17.

As shown in FIGS. 9-13 and 15-19, the upper portion of the clamp base member 104 may include a slot or cavity, and at least one aperture or indentation extending through a side wall of the clamp base member 104 and into the slot. The and at least one aperture or indentation may be offset from the binding aperture of the clamp base member 104. In some embodiments, the upper portion of the clamp base member 104 may at least a pair of apertures or indentations extending through a side wall of the clamp base member 104 on opposing sides of the aperture thereof (but not aligned with the binding aperture) thereof. As shown in FIGS. 9-19, the drivable clamp assemblies 110 may include a top clamp member 105 that is configured to mate or be positioned within the upper slot or cavity of the clamp base member 104. The top clamp member 105 may include a bearing aperture and at least one indentation, groove or slot that is aligned with the at least one aperture of the clamp base member 104 when the top clamp member 105 is positioned within the upper slot of the clamp base member 104 and the binding screw 103 extends through the bearing aperture of the clamp base member 104 and the top clamp member 105.

As shown in FIGS. 9-19, the binding screw 103 may be configured with a threaded portion that extends past the top clamp member 105 when the saddle 102 is positioned on the upper surface of the housing 101, the bottom surface of the clamp base member 104 is positioned on the upper surface of the saddle 102, and the top clamp member 105 is positioned within the upper slot of the clamp base member 104. In this way, the binding screw 103 may extend from within the top slot of the housing member and through the bearing apertures of the saddle 102, clamp base member 104 and the top clamp member 105, with the threaded portion extending past the top clamp member 105. As shown in FIGS. 9-19, the drivable clamp assemblies 110 may include a lock nut 6 is threadably engaged to the binding screw 103 to provide the positional locking and clamping force to apply a clamping or compressive force between the head of the binding screw 103 and the upper slot of the housing 101, between the saddle 102 and the clamp base member 104, and between the top clamp member 105 and the clamp base member 104. As shown in FIGS. 12 and 17, the drivable clamp assemblies 110 may include a spring 16 interspaced between the clamp top 105 and clamp base 104 to provisionally engage the surface roughness of the bottom surface of the clamp base 104 and the top surface of the saddle 102 and to provide an anti-rattle provision.

In this way, at least one bone or tissue fixation member 115, such as a pin, nail, wire (e.g., a k-wire) or any other bone or tissue fixation member, may be passed through the at least one aperture of the clamp base 104 and between the clamp base 104 and the clamp top 105 when the nut 106 is positioned on the binding screw 103 in a position that allows for sufficient space therebetween (in a direction extending along the axis of the binding screw 103). Before the nut 106 is tightened (and before or after at least one fixation member 115 positioned between the clamp base 104 and the clamp top 105), the clamp base 104 and the clamp top 105 may be rotated about the axis of the binding screw 103 to a particular orientation (e.g., about an axis perpendicular to the axis of the central bore of the housing and/or beam element 130 extending therethrough). The fixation members 115 may thereby be free to rotate 360 degrees in the plane that they lie. Similarly, before the nut 106 is tightened (and before or after at least one fixation member 115 positioned between the clamp base 104 and the clamp top 105), the entire upper clamp assembly may be rotated about the axis of the central bore of the housing 101 and/or a beam element 130 extending therethrough via the upper slot of the hosing 101 and the head portion of the binding screw 103. Still further, before or after the nut 106 is tightened (and before or after at least one fixation member 115 positioned between the clamp base 104 and the clamp top 105), the drivable clamp assembly 110, as a whole, may be translated along the axis of the beam element 130 via rotation of the drive member 107 when engaged with the engagement track 131 or by disengaging the drive member 107 from the engagement track 131. Once properly oriented and positioned, the nut 106 may be tightened down over the binding screw 103 to tightly and securely clamp the head of the binding screw 103 and the upper slot of the housing 101 together, the saddle 102 and the clamp base member 104 together, and the at least one fixation member 115 between the top clamp member 105 and the clamp base member 104, to form a secure and fixed construct.

Figure 26:
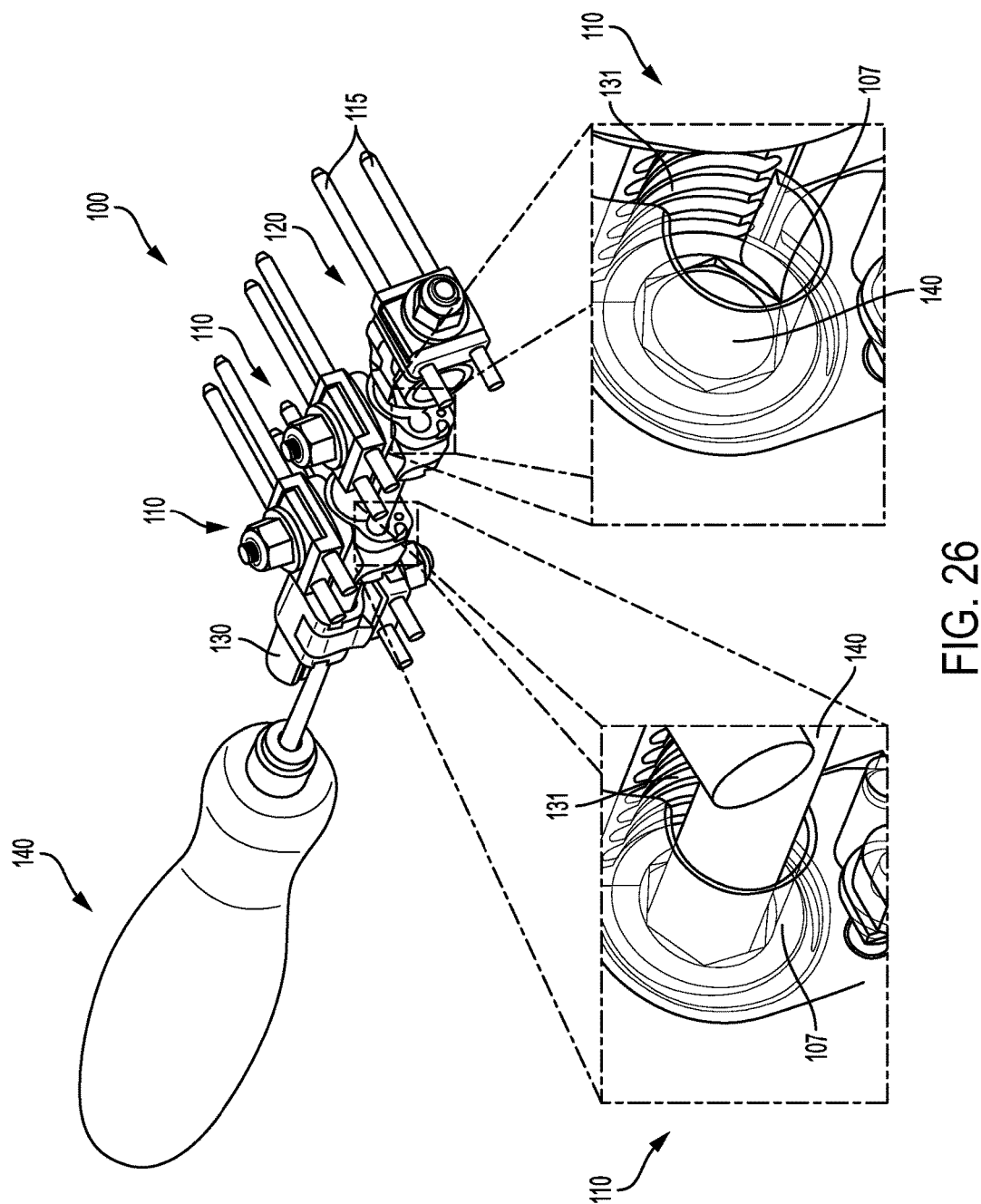
FIG. 26 is an elevational perspective view of the external fixation system of FIG. 1 illustrating a driving instrument engaging and driving a driving mechanism of a drivable clamp assembly.
Figure 27:
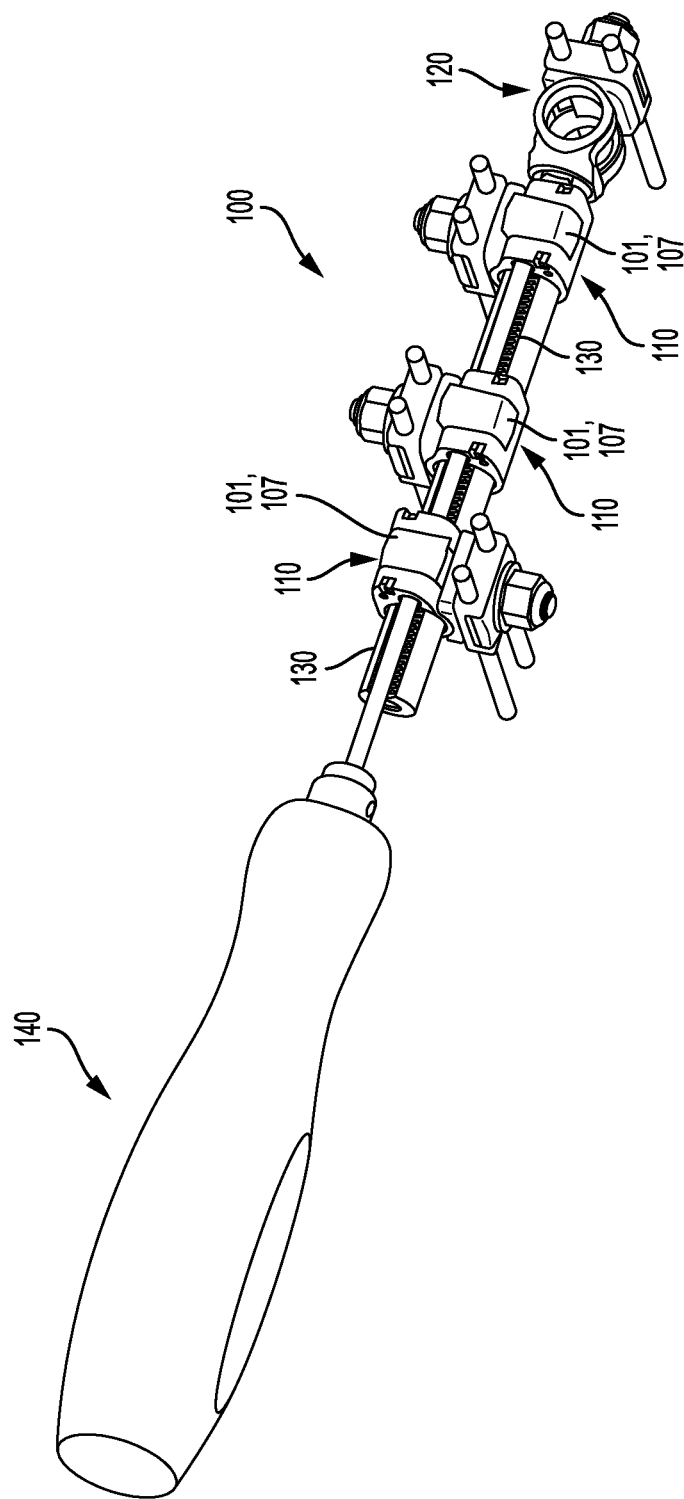
FIG. 27 is another perspective view of the external fixation system and driving instrument of FIG. 26.
Figure 28:
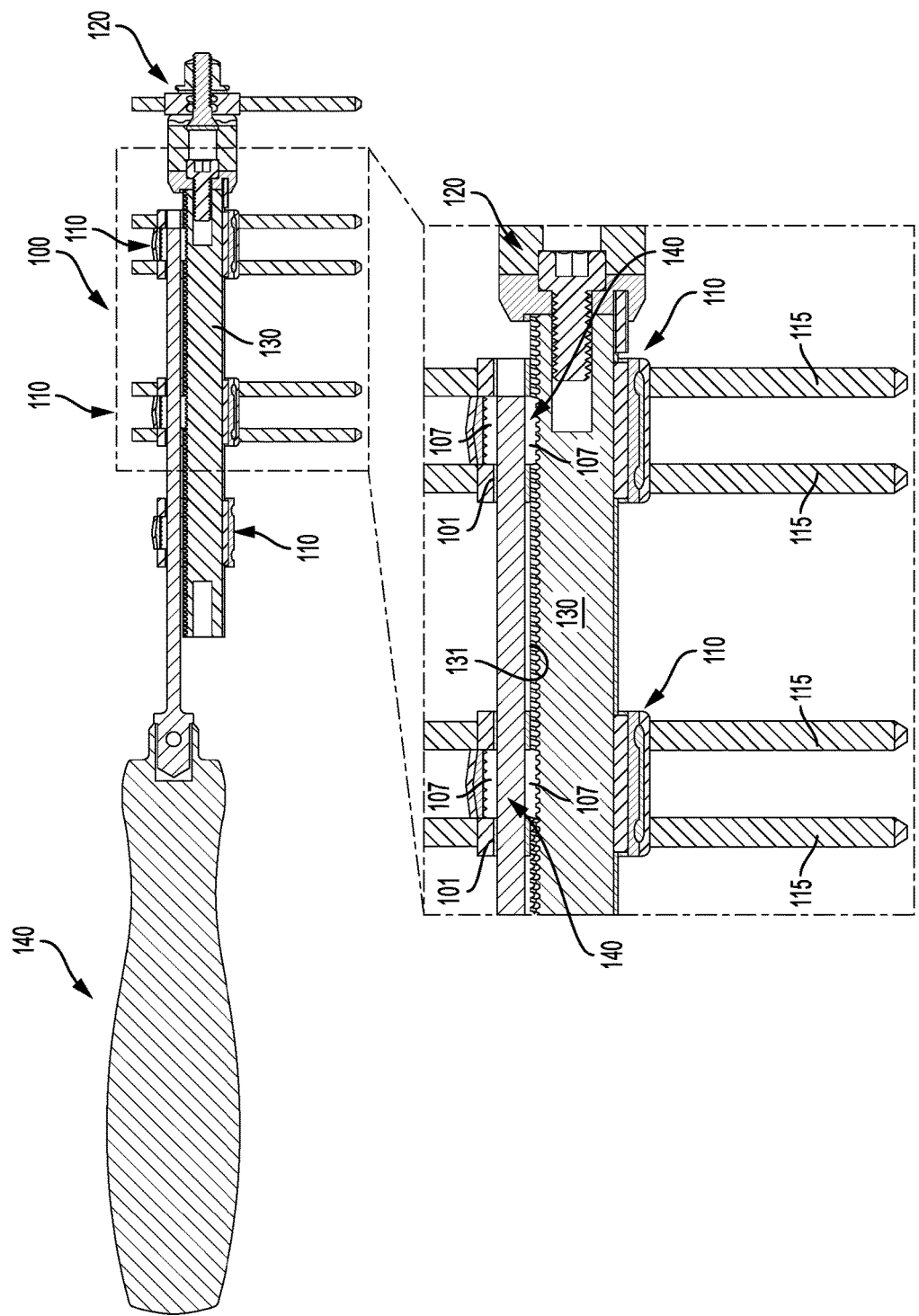
FIG. 28 is a cross-sectional view of the external fixation system and driving instrument of FIG. 26 illustrating engaged and disengaged drivable clamp assemblies.
Figure 29:
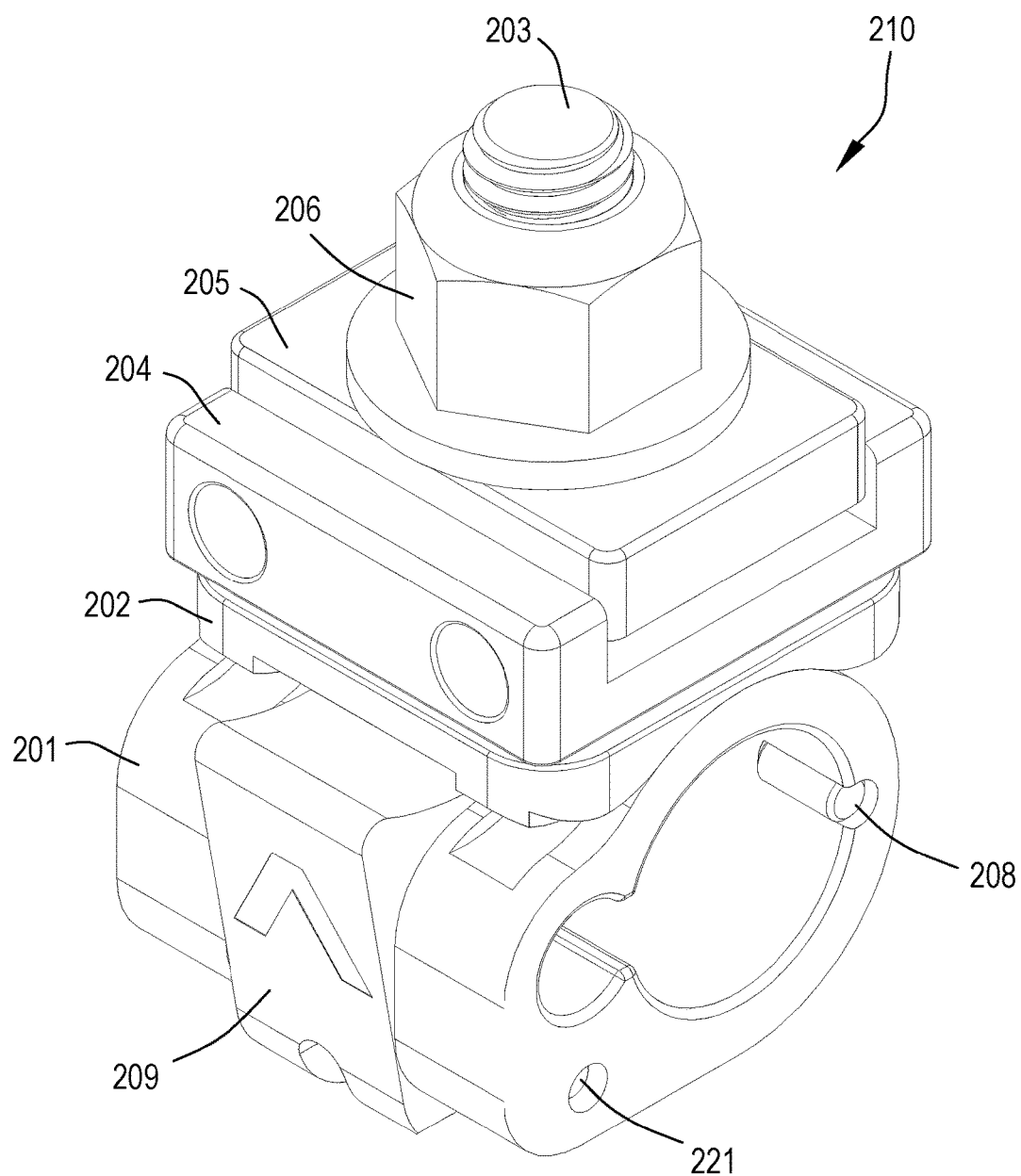
FIG. 29 is an elevational perspective view of another exemplary drivable clamp assembly of an external fixation system according to the present disclosure.
Figure 30:
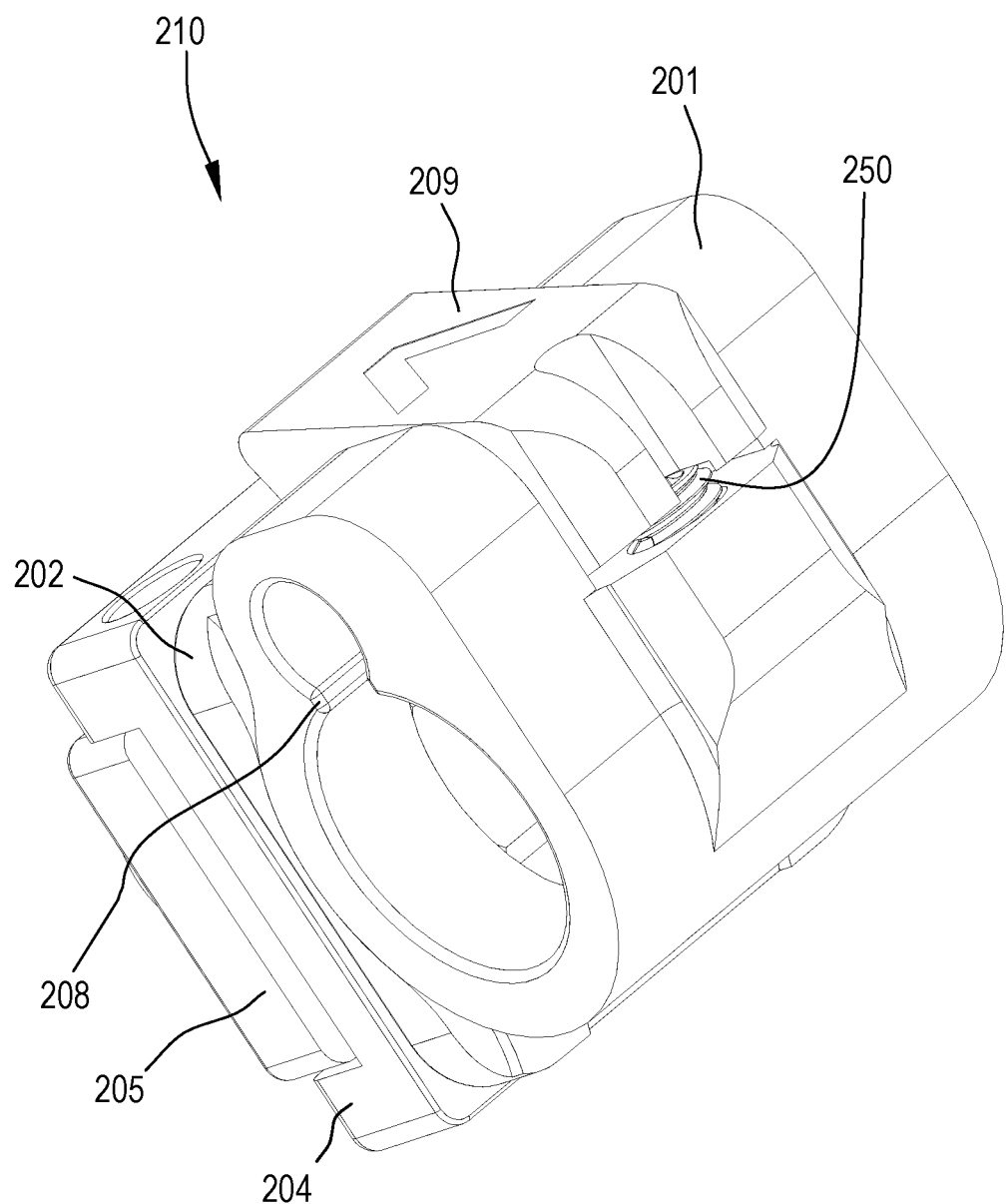
FIG. 30 is a bottom perspective view of the drivable clamp assembly of FIG. 29.
Figure 31:
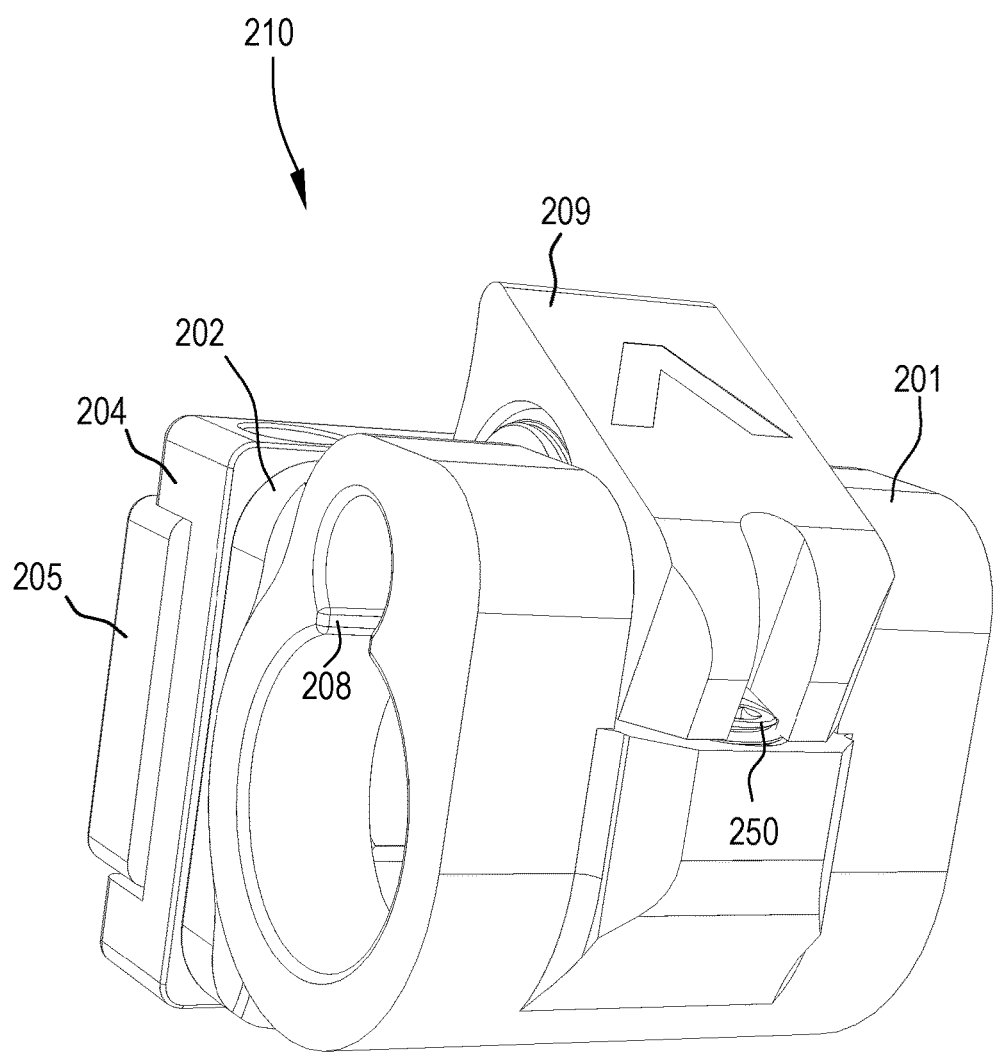
FIG. 31 is another bottom perspective view of the drivable clamp assembly of FIG. 29.
Figure 32:
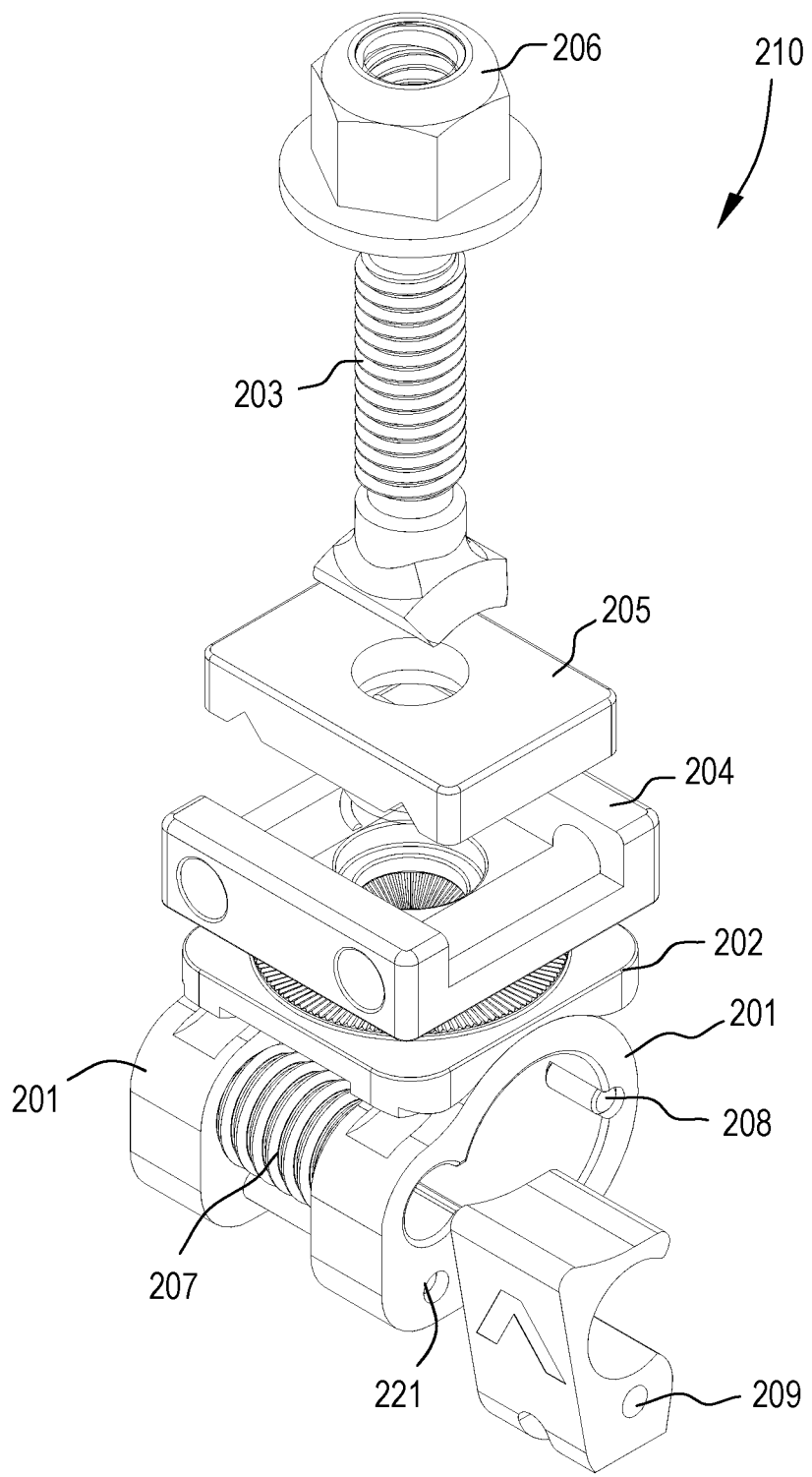
FIG. 32 is a perspective exploded view of the drivable clamp assembly of FIG. 29.
Figure 33:
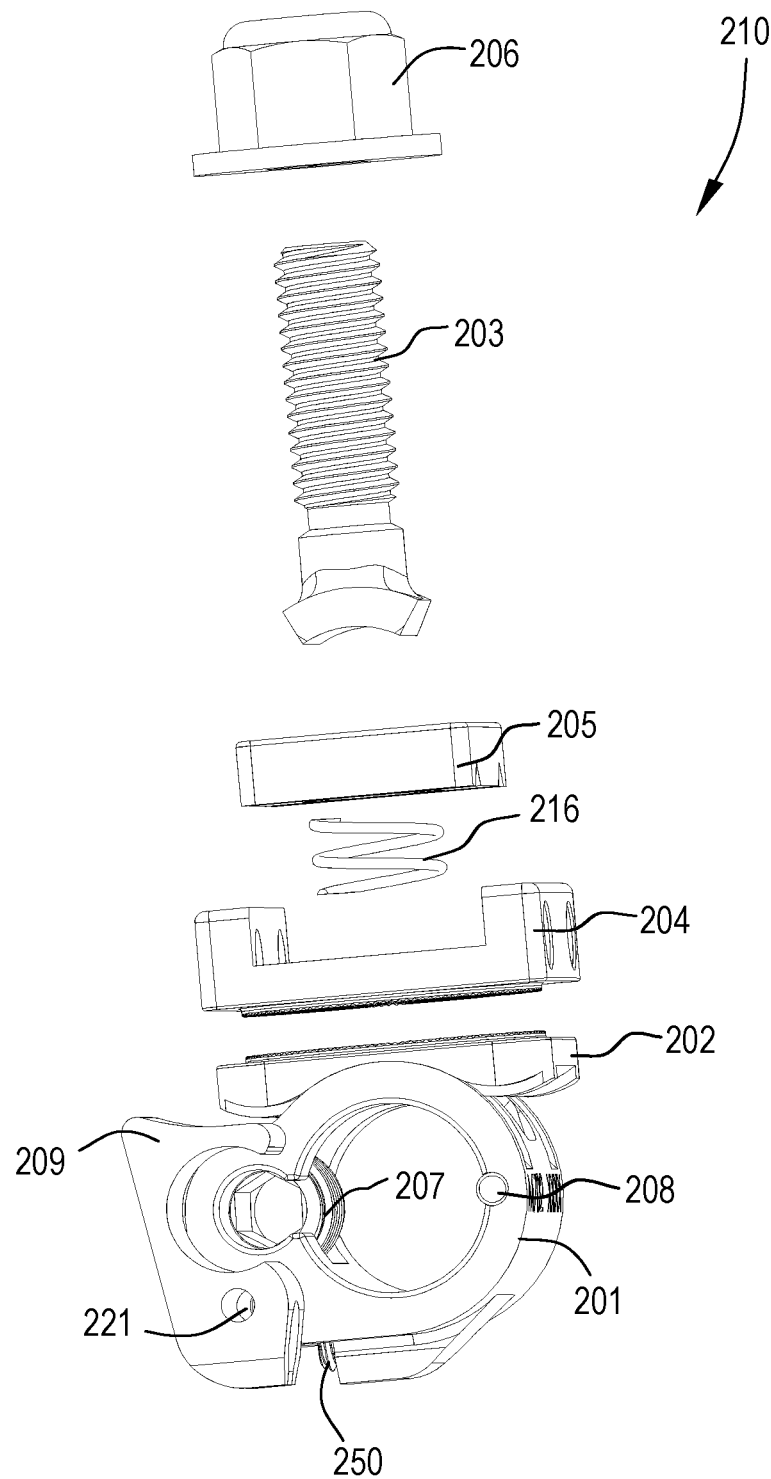
FIG. 33 is a side exploded view of the drivable clamp assembly of FIG. 29.
Figure 34:
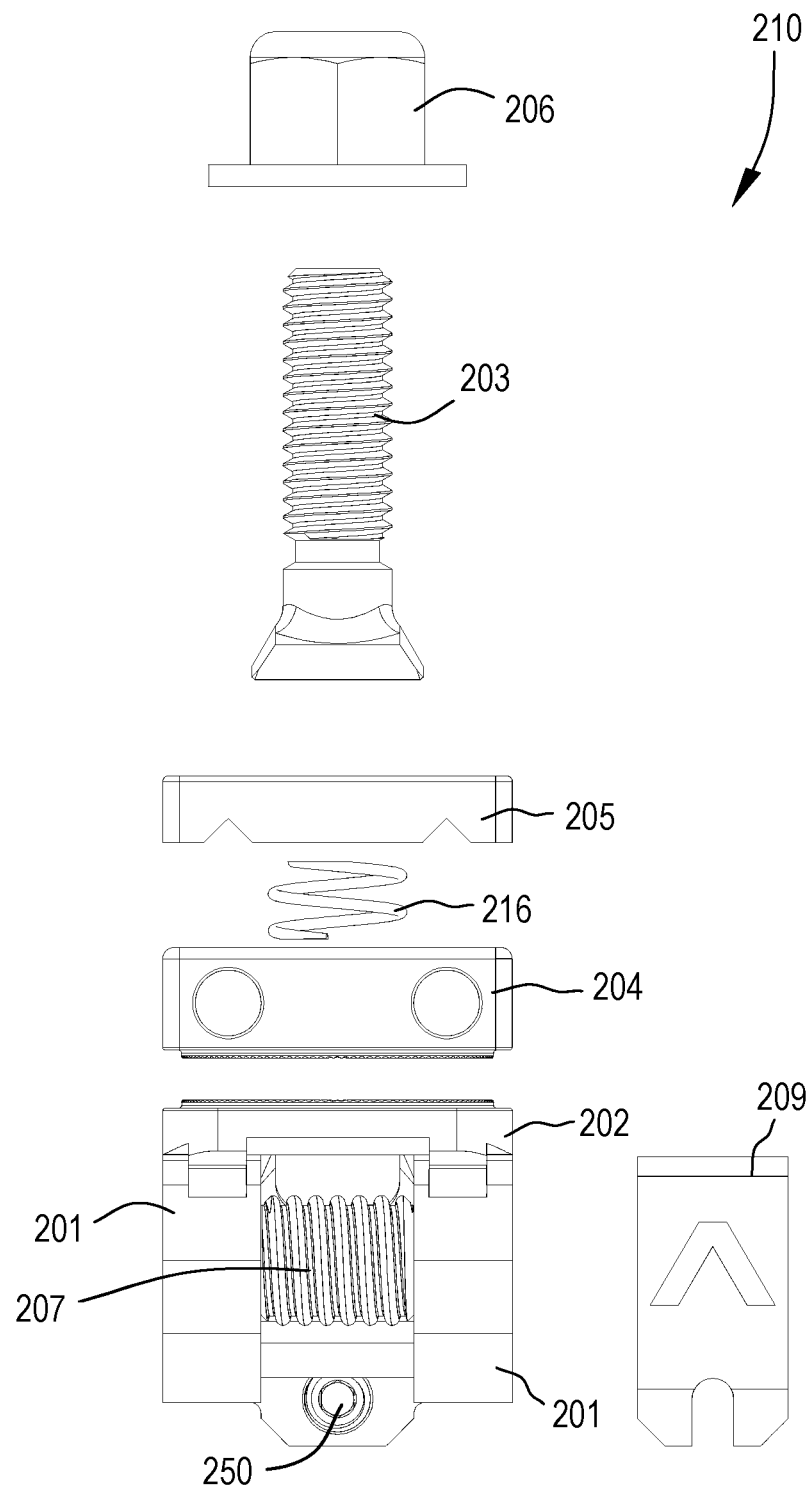
FIG. 34 is another side exploded view of the drivable clamp assembly of FIG. 29.

FIGS. 26-28 illustrate an exemplary embodiment of translating or driving the drivable clamp assemblies 110 axially along the axis of the beam element 130 when in the engaged state (i.e., the drive member 107 is engaged (threadably engaged) with the engagement track 131) via a driving mechanism 140. As shown in FIGS. 26-28, the drivable fixation assemblies 110 may be coupled to the beam element 130 such that the beam element 130 passes through the central bore of the housing 101. The alignment member 108 of the drivable clamp assemblies 110 also aligns the drivable clamp assemblies 110 about the axis of the beam element 130 such that the drive member 107 is aligned and engaged (threadably engaged) with the engagement track 131, as shown in FIGS. 26-28. As shown in FIGS. 26-28, with the drivable clamp assemblies 110 aligned or oriented about the axis of the beam element 130, the drive members 107 may be aligned along a common driving axis or the axis of rotation of the drive members 107.

Further, as shown in FIGS. 26-28 and discussed above, the drivable clamp assemblies 110 may be configured that the when in the engagement position or state, the driving aperture of the drive member 107 is positioned or aligned within the central bore of the housing 101 so that the driving aperture of the drive member 107 is accessible along the axis of the driving aperture or the drive member 107. In this way, as shown in FIGS. 26-28 an elongate driving tool or member 140 may be inserted through the drive member 107 of one or more proximate drivable clamp assemblies 110 to access a distal drivable clamp assembly 110 and engage and apply a torque thereto. In such an embodiment, a distal or driving portion of the driving instrument 140 may include a driving head configured to mate with the driving aperture of the drive member 107 of the drivable clamp assemblies 110 such that the driving instrument 140 is able to apply a torque or rotational force to the engaged drive member 107. The proximal portion of the drive member 107, extending between the distal or driving portion and a handle of the tool 140 for example, may include a cross-sectional shape and/or size that is smaller than driving aperture of the drive members 107 so that the proximal portion can extend through the one or more proximate drivable clamp assemblies 110, as shown in FIGS. 26-28. In this way, only the driving aperture of the drive member 107 that is engaged with the distal or driving portion of the driving instrument 140 may be rotated or torqued by the driving instrument 140 to effectuate axial translation of the distal drivable clamp assembly 110 along the beam element 130, while the proximate drivable clamp assemblies 110 are not translated or disturbed.

FIGS. 20-25 illustrate a rotatable end clamp assembly 120 that is configured to couple to an axial end of the beam element 130. The rotatable end clamp assembly 120 of FIGS. 20-25 is similar to the drivable clamp assemblies 110 of FIGS. 1-19 and 26-28, and therefore like reference numerals are used to indicate like features or aspects, and the description with respect to the drivable clamp assemblies 110 of FIGS. 1-19 and 26-28 directed thereto equally applies to rotatable end clamp assembly 120 of FIGS. 20-25 and is not repeated herein for brevity. The rotatable end clamp assembly 120 of FIGS. 20-25 may differ from the drivable clamp assemblies 110 of FIGS. 1-19 and 26-28 in that the end clamp assembly 120 is not suited to axially translate or drive along the beam element 130, but rather fix to an axial end of the beam element 130, as shown in FIGS. 1 and 2.

As shown in FIGS. 20-25, the housing 101 includes an aperture extending therethrough from a bottom surface of the housing 101 into the central bore. In some embodiments, the aperture extending into the central bore may be aligned or coaxial with the axis of the bearing screw 103. In some embodiments, the aperture extending into the central bore may be oriented substantially perpendicular to the axis of the central bore.

As shown in FIGS. 20-25, the rotatable end clamp assembly 120 may include a cap screw 122. The cap screw 122 may include a threaded shank and a head portion configured to effectuate rotation or torque of the cap screw 122. The aperture extending into the central bore of the housing 101 may be configured to allow the cap screw 122 to extend therethrough, as shown in FIGS. 20-25. For example, as shown in FIGS. 1 and 2 the cap screw 122 may extend into the end aperture 132 of the beam element 130. The cap screw 122 and the end aperture 132 of the beam element 130 may be configured to threadably mate to couple the end clamp assembly 120 to an end of the beam element 130, as shown in FIGS. 1 and 2. In this way, the axes of the beam element 130, the cap screw 122 bearing screw 103 may be aligned or coaxial (or may not be).

As also shown in FIGS. 20-25, the rotatable end clamp assembly 120 may include a spring pin or other anti-rotation member 123 configured to partially extend into an aperture or slot of the housing 101 and into the alignment groove 133 of the beam element 130 when the rotatable end clamp assembly 120 is coupled to an end of the beam element 130 via the cap screw 122. In this way, the anti-rotation member 123 may prevent at least the housing 101 of the rotatable end clamp assembly 120 from rotating about the axis of the beam element 130. It is noted that the remainder of the rotatable end clamp assembly 120 may be rotationally fixed about the axis of the beam element 130 via the anti-rotation member 123 if the nut 106 is tightened to effectively clamp the other components together.

FIGS. 29-36 illustrate another drivable clamp assembly 210 configured to axially translate along a beam element, such as the beam element 130 of FIGS. 1-8. The drivable clamp assembly 210 of FIGS. 29-36 is substantially similar to the drivable clamp assemblies 110 of FIGS. 1-19 and 26-28, and therefore like reference numerals proceeded by the numeral "2" are used to indicate like features or aspects, and the description with respect to the drivable clamp assemblies 110 of FIGS. 1-19 and 26-28 directed thereto equally applies to drivable clamp assembly 210 of FIGS. 29-36 and is not repeated herein for brevity. As shown in FIGS. 29-36, the drivable clamp assembly 210 differs from the drivable clamp assemblies 110 of FIGS. 1-19 and 26-28 in the how the engaged and disengage state of the drivable clamp assembly 210 and the driver or driving member 207 via the position of the release housing 209.

As shown in FIGS. 29-36 the release housing 209 of the drivable clamp assembly 210 is pivotably or rotatably coupled within the slot or aperture of the housing 201 via the pin or like mechanism 221. To effectuate the orientation or position of the housing 201 about its axis of rotation (e.g., pin 221), and thereby its positioned within (or exterior to) the central bore of the housing 201, the drivable clamp assembly 210 includes a set screw 250 threadably coupled to the housing 201, as shown in FIGS. 30, 31 and 33-36. The set screw 250 is selectively translatable along an axis that passes through a recess or bore of the housing 201 and is angled with respect to the axis of rotation of the release housing 209, as shown in FIGS. 29-36. In some embodiments, the set screw 250 is configured to selectively translate along an axis that is perpendicular to the axis of rotation of the release housing 209. The set screw 250 may threadably engage a portion of the housing 201 such that the set screw 250 is able to engage and exert a moment force to the release housing 209 about its axis of rotation.

Figure 35:
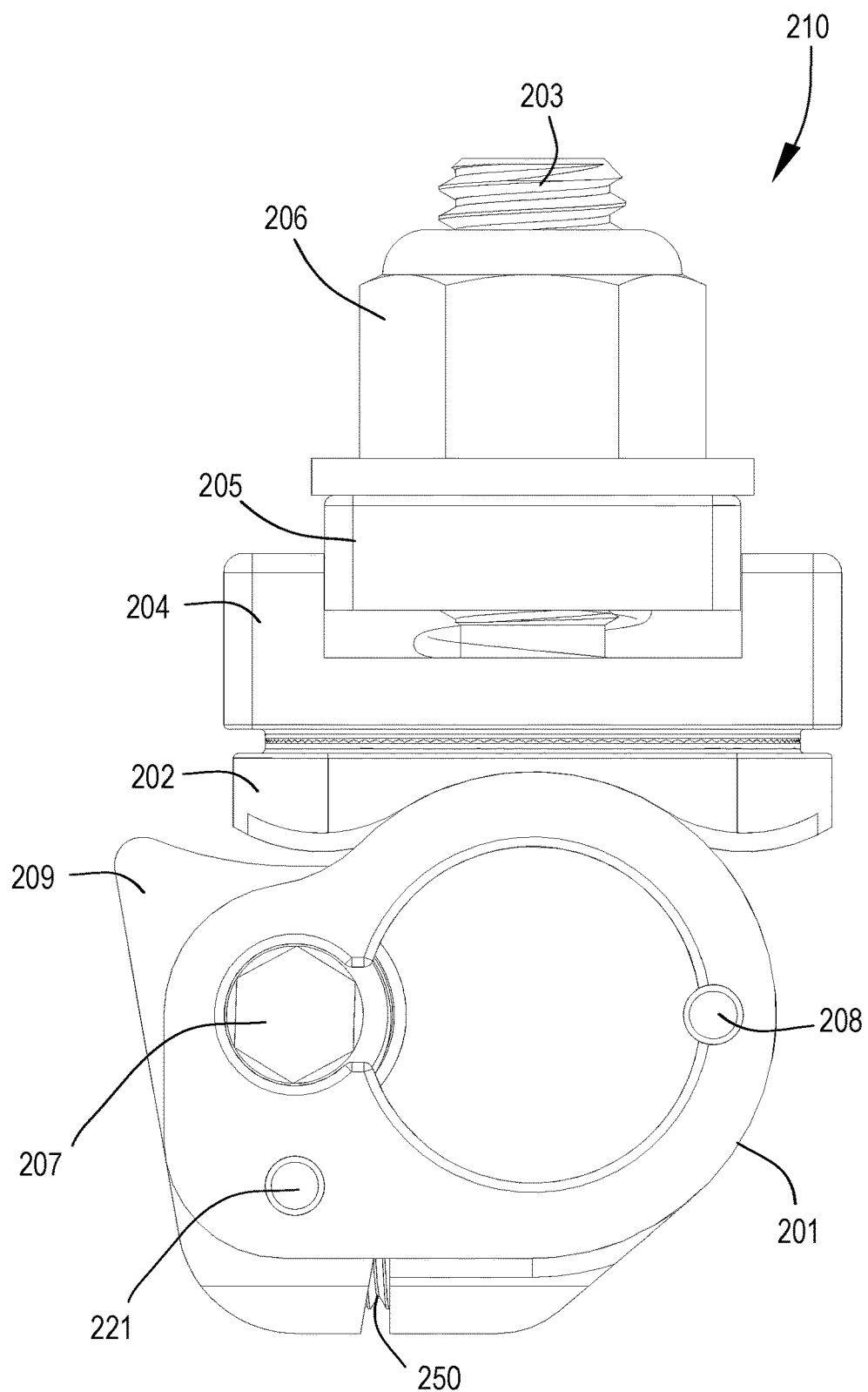
FIG. 35 is axial end view of the drivable clamp assembly of FIG. 29 in an engaged state.
Figure 36:
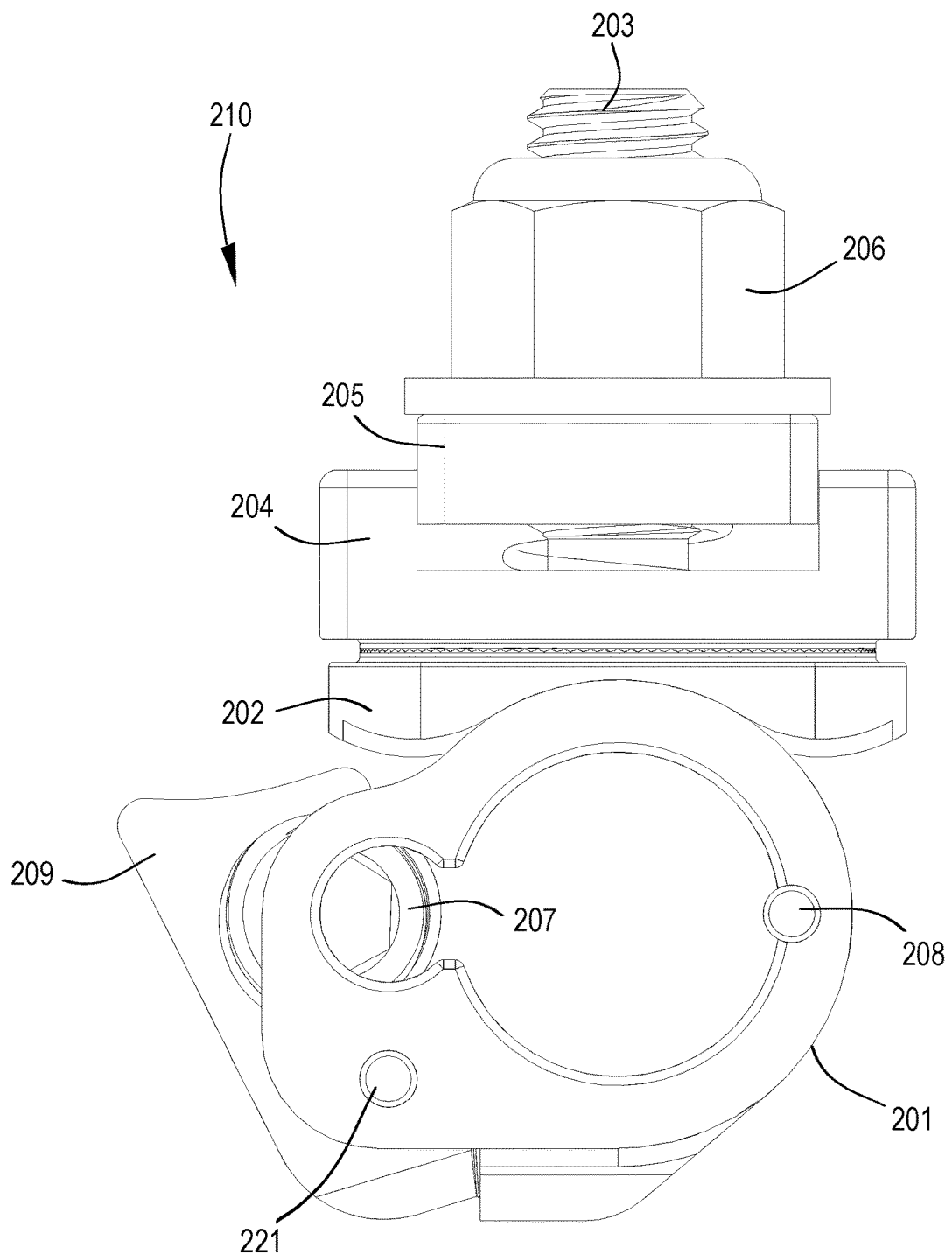
FIG. 36 is axial end view of the drivable clamp assembly of FIG. 29 in a disengaged state.
Figure 37:
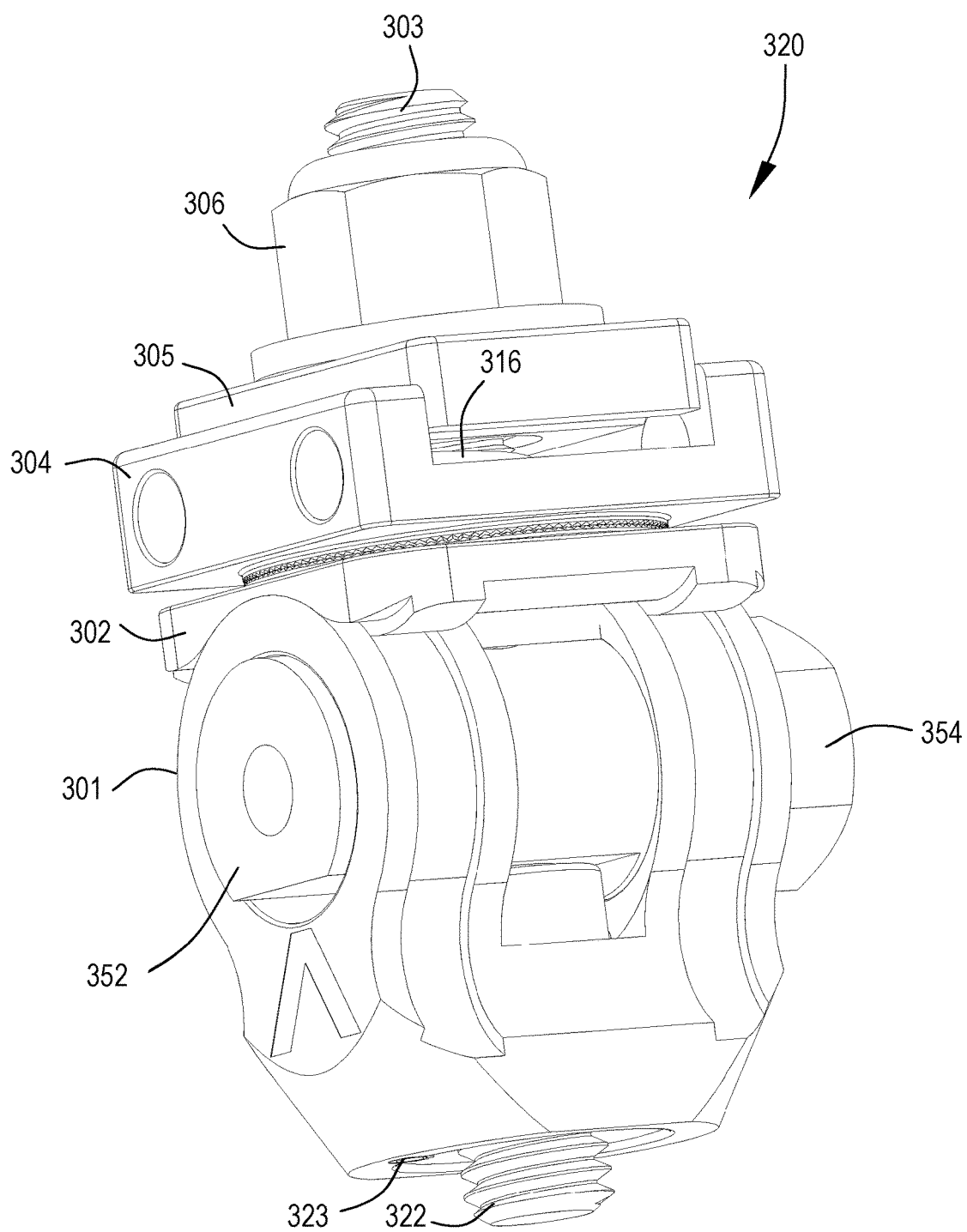
FIG. 37 is a perspective view of another exemplary end clamp assembly of an external fixation system according to the present disclosure.
Figure 38:
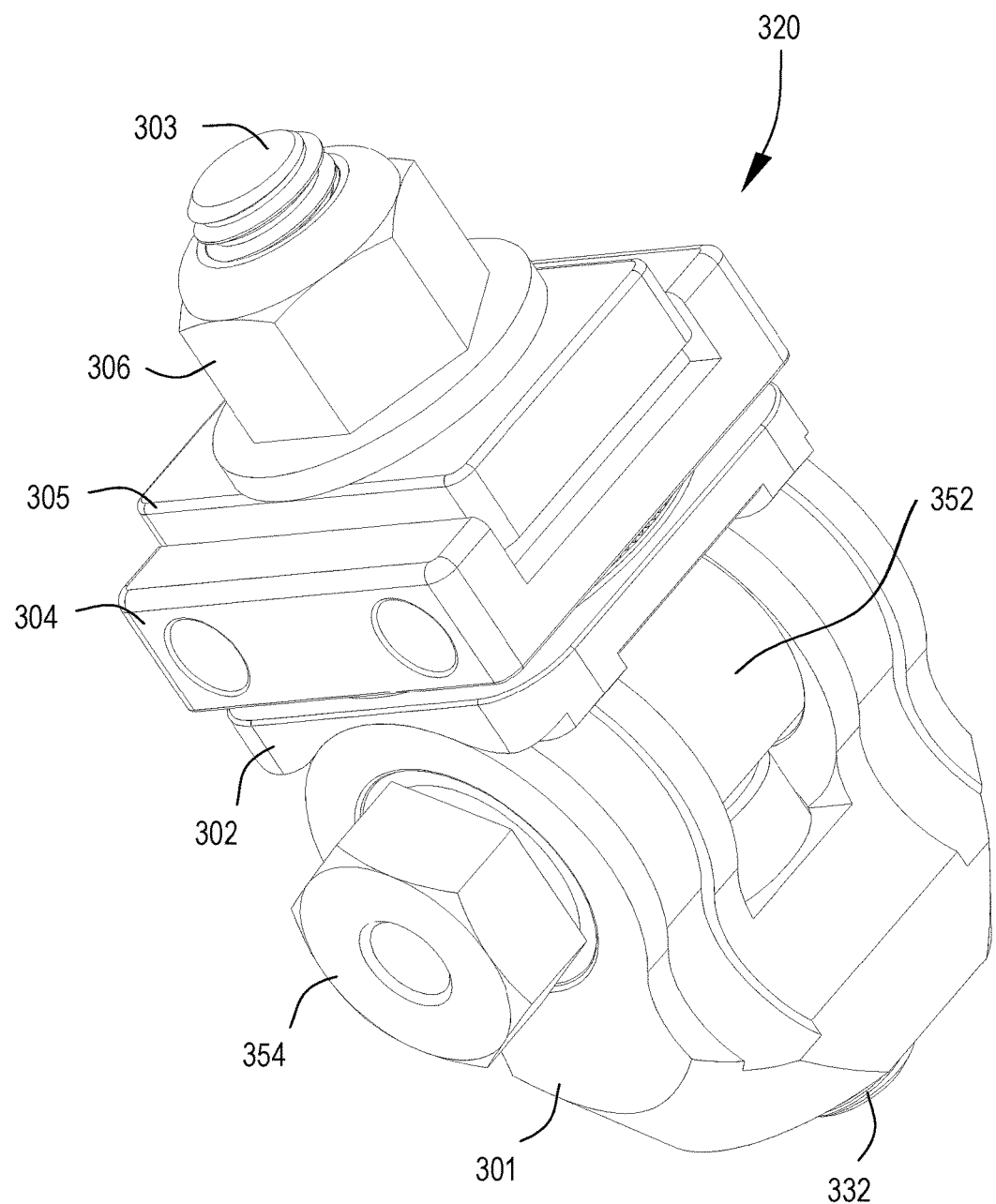
FIG. 38 is an elevational perspective view of the end clamp assembly of FIG. 37.
Figure 39:
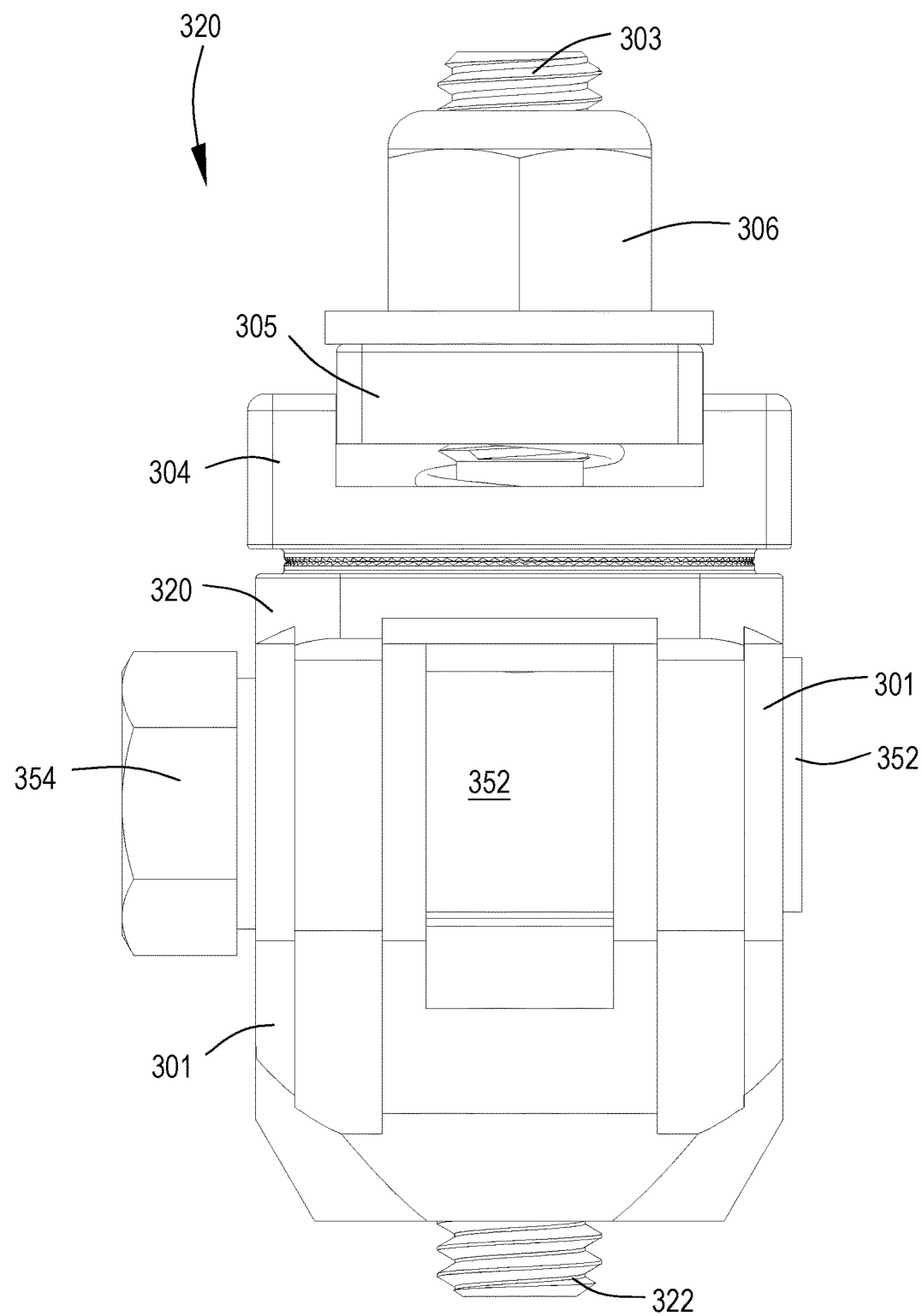
FIG. 39 is a side view of the end clamp assembly of FIG. 37.
Figure 40:
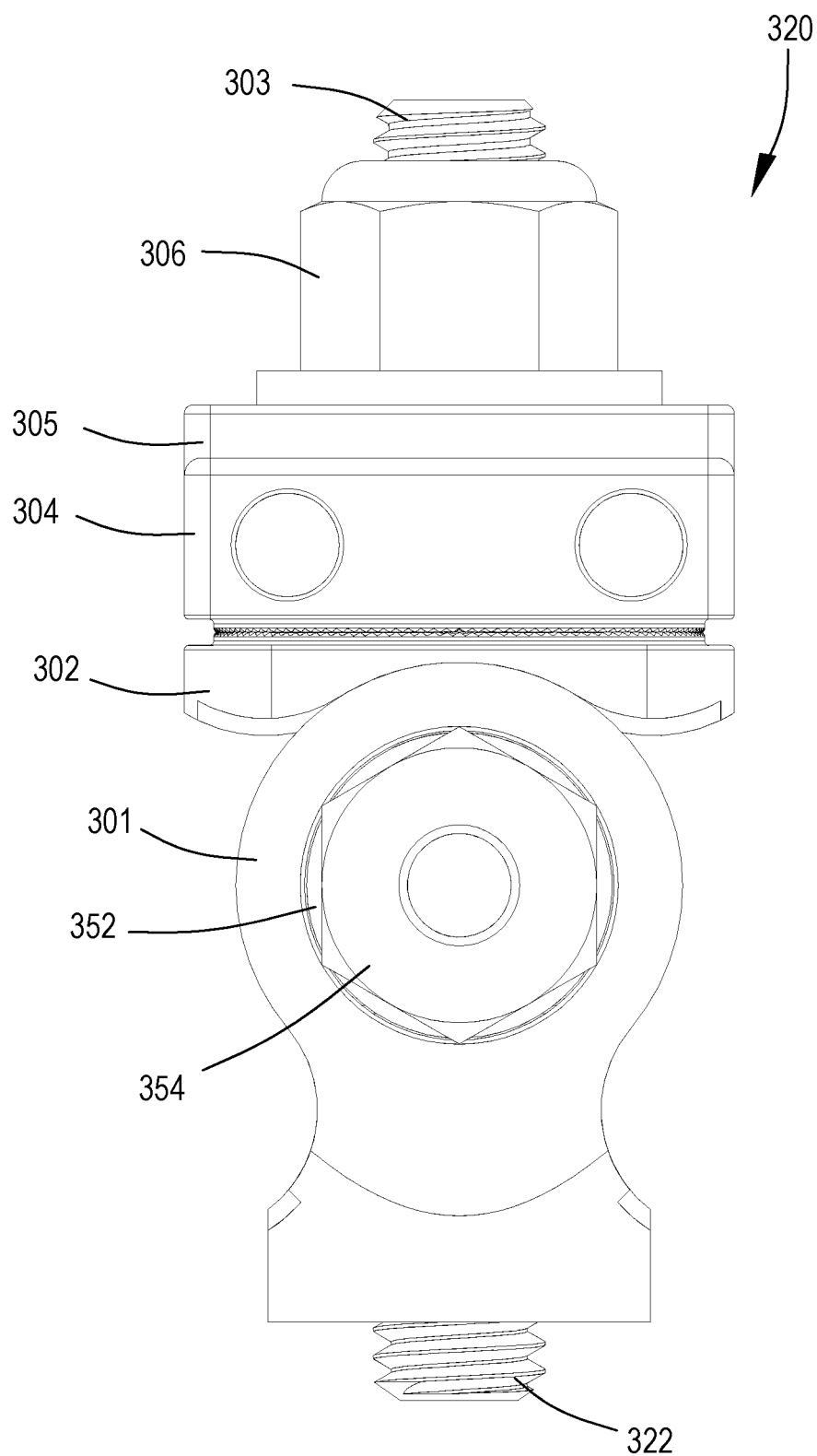
FIG. 40 is an axial end view of the end clamp assembly of FIG. 37.

As shown in FIGS. 29-36, the set screw 250 may threadably engage a bottom portion of the housing 201, and engage or abut a bottom portion of the release housing 209. However, the set screw 250 may be otherwise positioned or configured to engage or abut a differing portion of the release housing 209. The set screw 250 may include any configuration or arrangement that effectuates a moment force to the release housing 209 about its axis of rotation along the axis or path of movement of the set screw 250. For example, as the illustrated set screw 250 engages a bottom portion of the release housing 209 such that the axis of rotation of the release housing 209 is positioned between the portion engaged by the set screw 250 and the central bore of the housing 201 and the driver member 207, axial movement of the set screw 250 out of the housing 201 will effectuate rotation of the release housing 209, and thereby the driver member 207, into the central bore of the housing 201. In this way, the set screw 250 may be torqued or selectively translated to a position (e.g., an extended or retracted position, depending upon is position) such that the drivable clamp assembly 210 is in the engaged state with the driver member 207 biased into the central bore (via rotation of the release housing about its axis of rotation) and engaging (e.g., threadably engaging) the engagement track of a beam element passing through the central bore of the housing, as shown in FIG. 35 and explained above. Similarly, the set screw 250 may be torqued or selectively translated to a position (e.g., an extended or retracted position, depending upon is position) such that the drivable clamp assembly 210 is in the disengaged state with the driver member 207 biased or translated at least partially out of the central bore (via rotation of the release housing about its axis of rotation) and disengaged (e.g., threadably disengaged) from the engagement track of a beam element passing through the central bore of the housing, as shown in FIG. 36 and explained above.

FIGS. 37-44 illustrate another rotatable end clamp assembly 320 configured to couple to an axial end of a beam element, such as the beam element 130 of FIGS. 1-8. The rotatable end clamp assembly 320 of FIGS. 37-44 is substantially similar to the rotatable end clamp assemblies 120 of FIGS. 1-3 and 20-28, and therefore like reference numerals proceeded by the numeral "3" are used to indicate like features or aspects, and the description with respect to the rotatable end clamp assemblies 210 of FIGS. 1-3 and 20-28 directed thereto equally applies to rotatable end clamp assembly 320 of FIGS. 37-44 and is not repeated herein for brevity. As shown in FIGS. 37-44 the rotatable end clamp assembly 320 differs from the rotatable end clamp assembly 120 of FIGS. 1-3 and 20-28 in the inclusion of a clamp guide 352 and a clamp screw 354 within the central bore of the housing 301.

Figure 41:
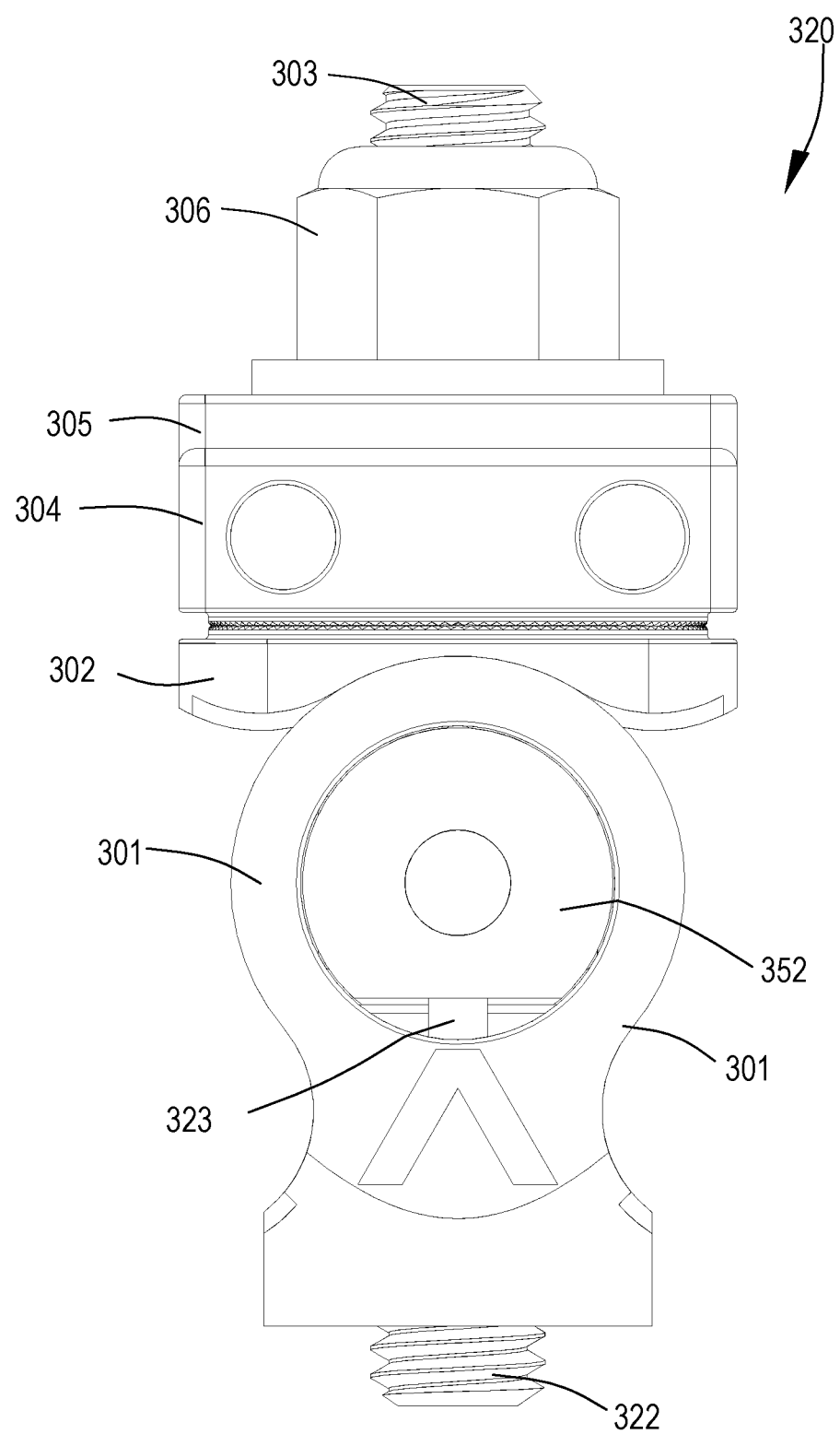
FIG. 41 is another axial end view of the end clamp assembly of FIG. 37.
Figure 42:
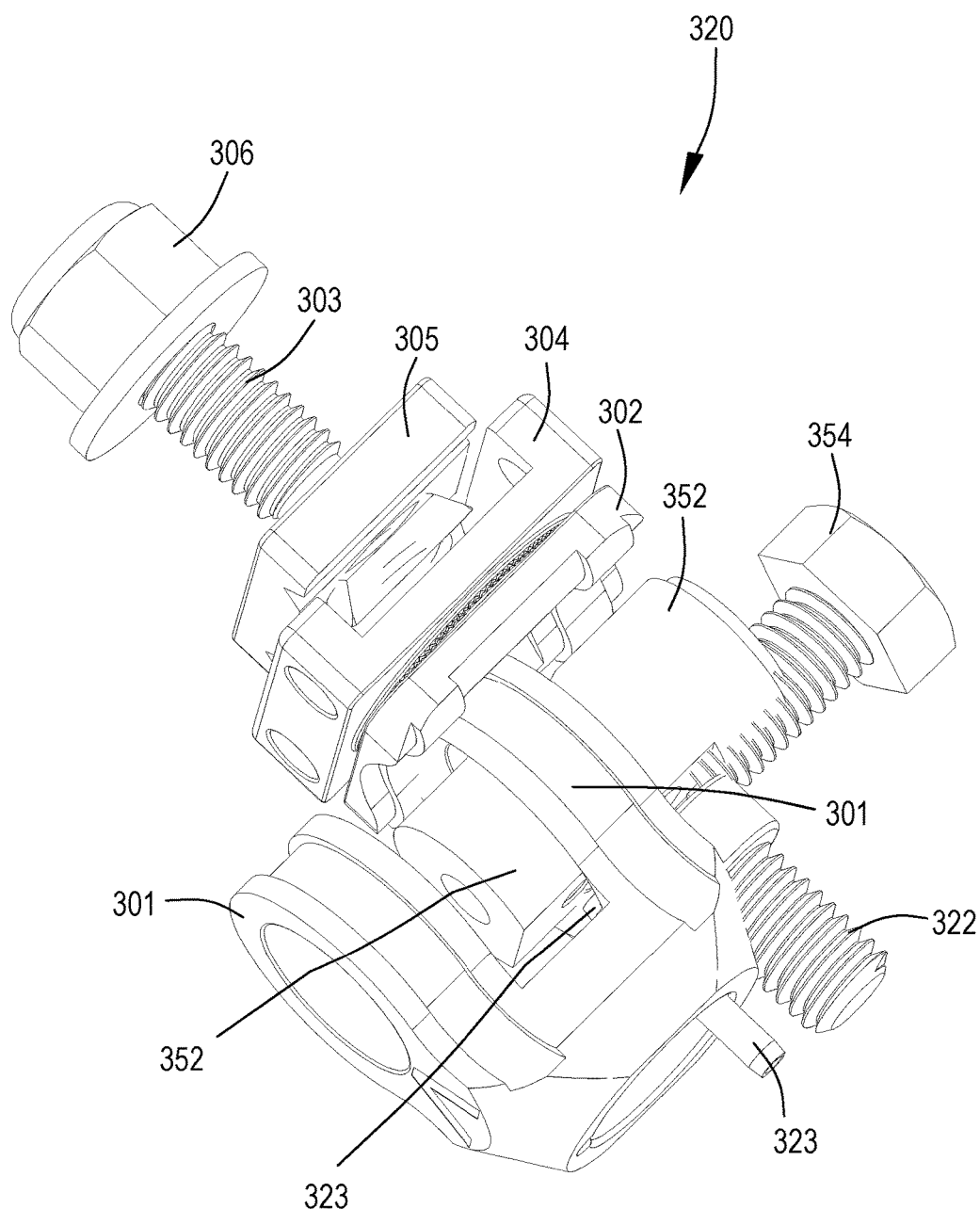
FIG. 42 is an elevational partial exploded view of the end clamp assembly of FIG. 37.
Figure 43:
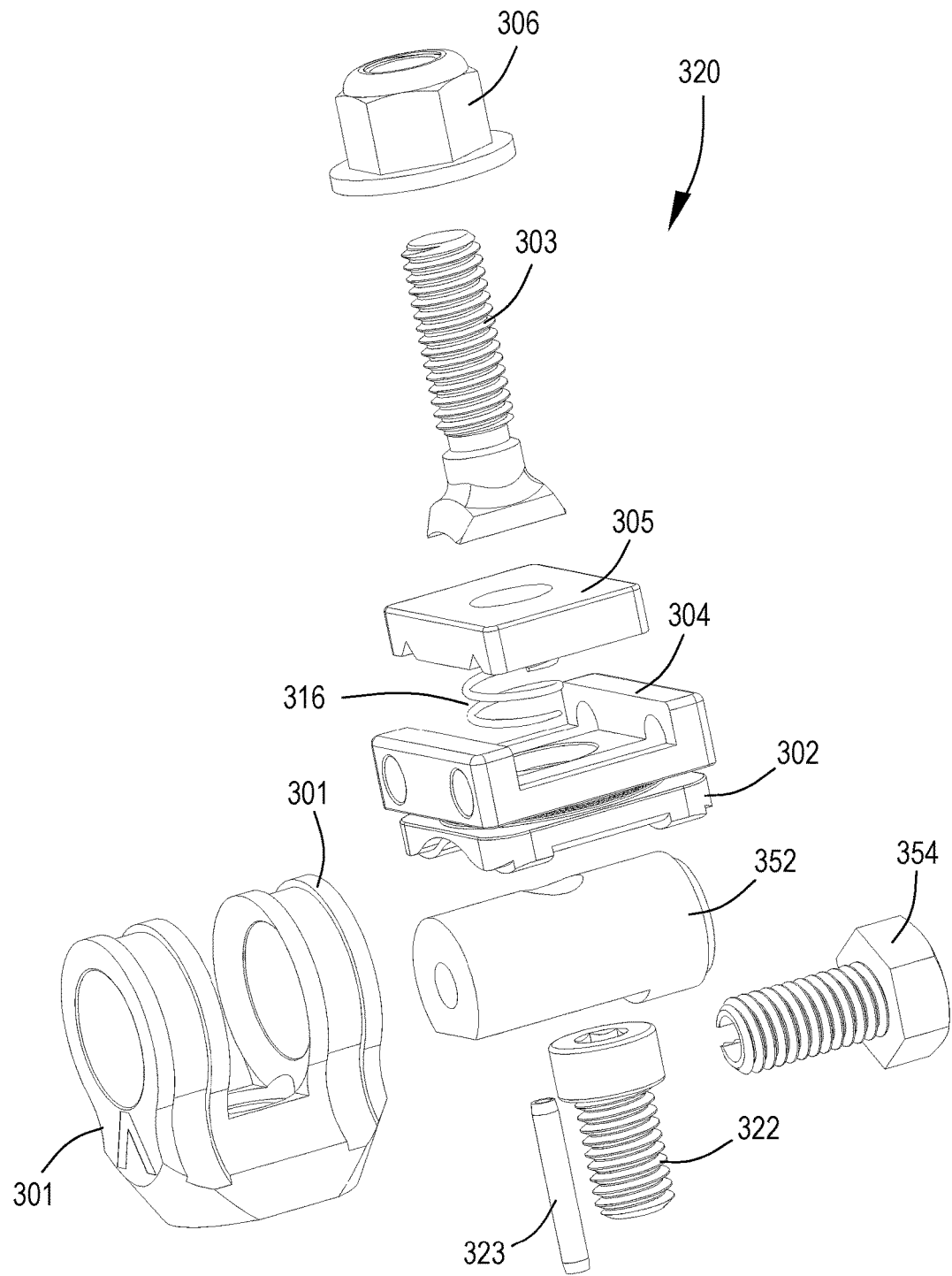
FIG. 43 is an elevational exploded view of the end clamp assembly of FIG. 37.
Figure 44:
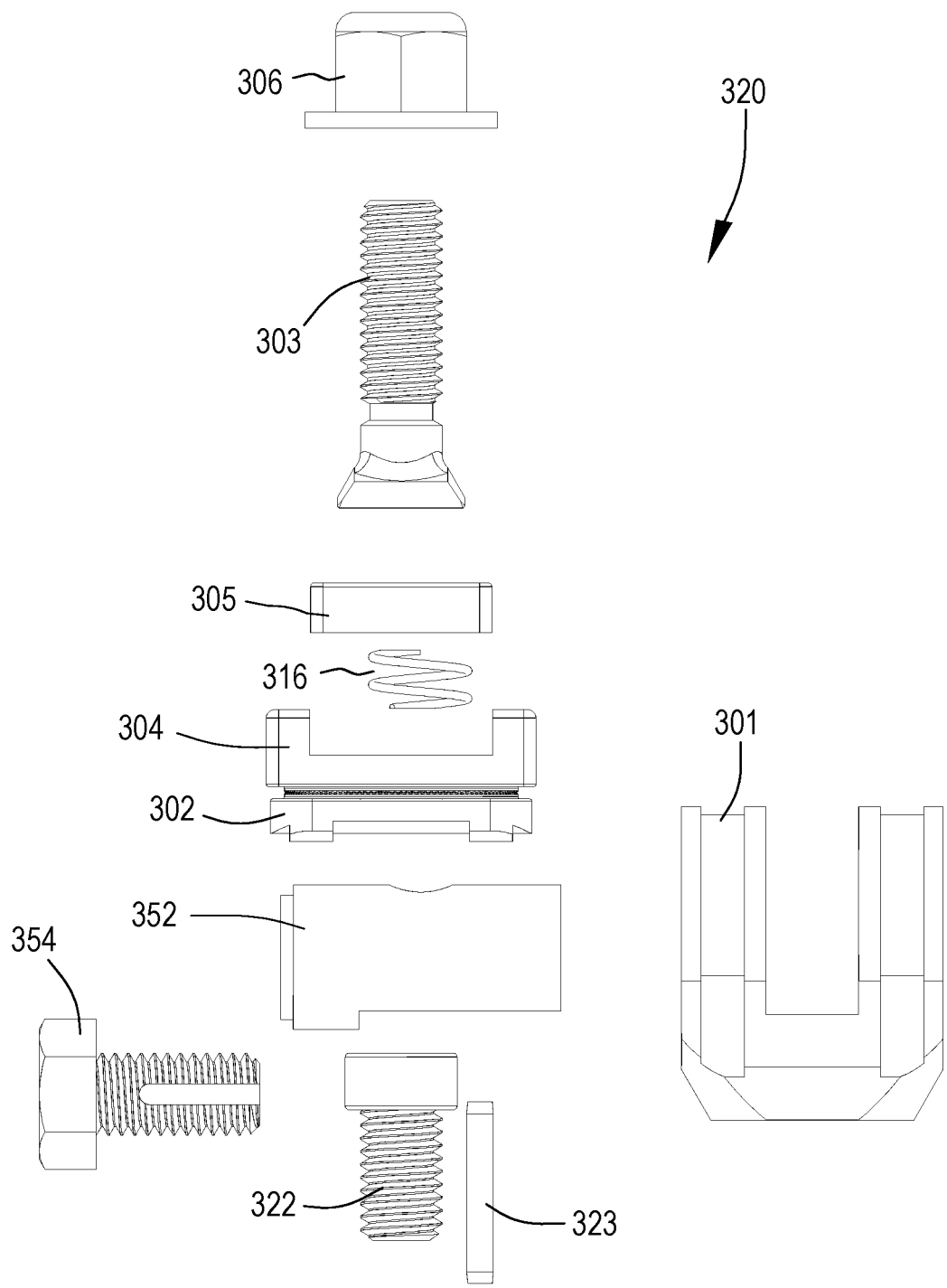
FIG. 44 is a side exploded view of the end clamp assembly of FIG. 37.

As shown in FIGS. 37-44, the rotatable end clamp assembly 320 may include a clamp guide 352 fixed within the central bore of the housing 301. As shown in FIGS. 37-44, the clamp guide 352 may be generally cylindrical and a bore or aperture, such as a central bore. In some embodiments, the aperture extending within or through the clamp guide 352 may be aligned or coaxial with, or parallel but offset to, the axis of the central bore of the housing 301, as shown in FIG. 41. As shown in FIGS. 37-44, clamp guide 352 may include a flat, groove or otherwise be configured to extend over the cap screw 322 extending through aperture of the housing 301 and into the end aperture of an end of a beam element, as explained above. The clamp guide 352 may for securely within the central bore of the housing 301 such that radial movement therein is prevented or at least minimized. Axial translation of the clamp guide 352 from within the central bore of the housing 301 may be prevented by a step portion abutting the head of the cap screw 122, the clamp guide 352 being larger than the openings at the axial ends of the central bore, the clamp screw 354 being coupled to the clamp guide 352 and being slightly larger than an opening at an axial end of the central bore, and/or the anti-rotation member 323 extending into an aperture of bore of the clamp guide 352 (see FIGS. 41 and 42). Similarly, rotational translation of the clamp guide 352 within the central bore of the housing 301 may be prevented by the flat of the bottom surface of the clamp guide 352 abutting the cap screw 322, the shape of the mating surfaces of the clamp guide 352 and the central bore of the housing 301, and/or the anti-rotation member 323 extending into an aperture of bore of the clamp guide 352 (see FIGS. 41 and 42).

As shown in FIGS. 37-44, the clamp screw 354 may couple within the axially extending aperture of the clamp guide 352. As also shown in FIGS. 37-44, the clamp screw 354 may include external threads, an axially extending bore or aperture extending therethrough, and an axially extending slot, groove or the like extending at least partially radially through the clamp screw 354 to the axially extending through aperture thereof. The axially extending aperture of the clamp guide 352 may include internal threads to threadably mate with the enteral threads of the clamp screw 354, for example. The axially extending aperture of the clamp guide 352 may also narrow at it extends axially through the clamp guide 352. In some embodiments, the axially extending aperture of the clamp guide 352 may narrow along one axial direction through the clamp guide 352. In some embodiments, the axially extending aperture of the clamp guide 352 may narrow along both axial directions through the clamp guide 352 from the axial ends thereof toward the medial portion of the clamp guide 352.

The clamp guide 352 and the clamp screw 354 may be configured such that when the clamp screw 354 is axially translated into the axially extending narrowing aperture of the clamp guide 352, the clamp guide 352 effectuates a radially compressive force to the clamp screw 354. In some embodiments, the radially compressive force applied by the clamp guide 352 to the clamp screw 354 effectuates compression of the axially extending aperture of the clamp screw 354 via the slot therein. In this way, a fixation member, such as a pin, nail, wire (e.g., a k-wire) or any other bone or tissue fixation member, may extend through the clamp screw 354, the clamp guide 352 and the housing 301 and locked or fixed at a particular location via transition of the clamp screw 354 into the clamp guide 352. The rotatable end clamp assembly 320 may thereby removably couple to another fixation member.

It is to be understood that the above description is intended to be illustrative, and not restrictive. Numerous changes and modifications may be made herein by one of ordinary skill in the art without departing from the general spirit and scope of the disclosure as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably connected" is used herein to refer to both connections resulting from separate, distinct components being directly or indirectly coupled and components being integrally formed (i.e., monolithic). Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the disclosure has been described in detail in connection with only a limited number of embodiments, it should be readily understood that the disclosure is not limited to such disclosed embodiments. Rather, the disclosure can be modified to incorporate any number of variations, alterations, substitutions or equivalent arrangements not heretofore described, but which are commensurate with the spirit and scope of the disclosure. Additionally, while various embodiments of the disclosure have been described, it is to be understood that aspects of the disclosure may include only some of the described embodiments. Accordingly, the disclosure is not to be seen as limited by the foregoing description, but is only limited by the scope of the appended claims.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. An external bone or tissue fixation system, comprising, an elongate beam element defining an axis and comprising an axially extending threaded track portion; and
at least one drivable fixation clamp assembly comprising a main housing with a central bore, a driving housing rotatably coupled within an opening of the main housing, a threaded driving member in communication with the driving housing, and a clamp assembly selectively rotatably coupled to the main housing configured to clamp to at least one fixation member,
wherein the elongate beam element extends axially through central bore of the main housing,
wherein the driving member is movable with respect to the central bore via rotation of the driving housing between an engaged state with the threaded track portion and a disengaged state from the threaded track portion, and
wherein rotation of the driving member in the engaged state axially translates the at least one drivable fixation clamp assembly along the beam element.

2. The external fixation system of claim 1, wherein the beam element includes an axially extending alignment groove, and wherein the central bore of the least one drivable fixation clamp assembly includes an anti-rotation member that extends into the alignment groove to rotationally fix the least one drivable fixation clamp assembly and the beam element about the axis of the beam element.

3. The external fixation system of claim 2, wherein the at least one drivable fixation clamp assembly comprises a plurality of drivable fixation clamp assemblies axially positioned along the beam element.

4. The external fixation system of claim 3, wherein the alignment groove of the beam element and the anti-rotation members of the plurality of drivable fixation clamp assemblies position the plurality of drivable fixation clamp assemblies about the axis of the beam element such that the driving members are coaxial.

5. The external fixation system of claim 4, wherein the driving members include a through aperture extending axially therethrough, and wherein the through apertures of the plurality of drivable fixation clamp assemblies are fully positioned within the central bore of the respective main housing in the engaged state.

6. The external fixation system of claim 1, wherein the driving member includes a through aperture extending axially therethrough, and wherein the through aperture of the driving member is fully positioned within the central bore of the main housing in the engaged state.

7. The external fixation system of claim 6, wherein the through aperture of the driving member is configured to mate with a driving portion of a driving tool to effectuate rotation of the driving member.

8. The external fixation system of claim 7, further comprising the driving tool, and wherein the driving tool comprises a proximate portion that is configured to pass through the through aperture of the driving member.

9. The external fixation system of claim 1, wherein the clamp assembly is selectively rotatable partially about the axis of the beam element.

10. The external fixation system of claim 1, wherein the clamp assembly is selectively rotatable about an axis that extends perpendicular to the axis of the beam element.

11. The external fixation system of claim 1, wherein the clamp assembly comprises a bearing screw with a head portion positioned within a slot of the main housing.

12. The external fixation system of claim 11, wherein the slot of the main housing extends partially about the axis of the beam element.

13. The external fixation system of claim 11, wherein the clamp assembly further comprises a saddle member in abutment with a first portion of the outer surface of the main housing.

14. The external fixation system of claim 13, wherein the first portion of the outer surface of the main housing extends partially about the axis of the beam element.

15. The external fixation system of claim 13, wherein the clamp assembly further comprises a clamp base member in abutment with the saddle member, and a clamp top member positioned on an opposing side the clamp base member than the saddle member, and wherein the clamp assembly is configured to clamp to the at least one fixation member between the clamp top member and the clamp base member.

16. The external fixation system of claim 15, wherein mating surfaces of the clamp base member and the saddle member include a friction increasing profile.

17. The external fixation system of claim 13, wherein the bearing screw extends through the saddle member, the clamp base member and the clamp top member such that a threaded portion extends past the clamp top member, and wherein the clamp assembly further comprises a nut threadably engaged with the threaded portion of the bearing screw.

18. The external fixation system of claim 17, wherein translation of the nut along the bearing screw towards the head portion effectuates a compressive force to the at least one fixation member when positioned between the clamp top member and the clamp base member.

19. The external fixation system of claim 17, wherein translation of the nut along the bearing screw towards the head portion effectuates a compressive force to the main housing between the head portion of the bearing screw and the saddle member to rotationally fix the clamp assembly about the axis of the beam element.

20. The external fixation system of claim 17, wherein translation of the nut along the bearing screw towards the head portion effectuates a compressive force between the saddle member and the clamp base member to rotationally fix the clamp base member and the clamp top member about the bearing screw.

21. The external fixation system of claim 1, wherein the driving housing is rotationally fixed to the main housing in the engaged state via at least one movable pin that extends within the driving housing and the main housing and is offset from the axis of rotation of the driving housing.

22. The external fixation system of claim 21, wherein removal of the at least one movable pin from the driving housing or the main housing effectuates the disengaged state.

23. The external fixation system of claim 1, wherein the driving housing is rotationally fixed with respect to the main housing in the engaged state via at least one set screw extending between the main housing and the driving housing.

24. The external fixation system of claim 23, wherein the at least one set screw is axially translatable within the main housing along a direction that is angled with respect to the axis of rotation of the driving housing.

25. The external fixation system of claim 23, wherein the at least one set screw is axially translatable within the main housing along a direction that is perpendicular with respect to the axis of rotation of the driving housing.

26. The external fixation system of claim 23, wherein the at least one set screw is axially translatable between a first position that rotates the driving housing such that the driving member is moved at least partially into the central bore and into the engaged state, and a second position that allows the driving housing to rotate such that the driving member is moved at least partially out of the central bore and into the disengaged state.

27. The external fixation system of claim 1, further comprising at least one end fixation clamp assembly fixed to an axial end of the beam element.

28. The external fixation system of claim 27, wherein the at least one end fixation clamp assembly is axially fixed to the axial end of the beam element.

29. The external fixation system of claim 27, wherein the at least one end fixation clamp assembly comprises a second main housing with a second central bore, and a second clamp assembly selectively rotatably coupled to the second main housing configured to clamp to at least one second fixation member.

30. The external fixation system of claim 29, wherein the at least one end fixation clamp assembly is fixed to the axial end of the beam element via a cap screw extending through the second main housing and threadably engaged within an internally threaded aperture extending axially within the beam element from the axial end thereof.

31. The external fixation system of claim 29, wherein the at least one end fixation clamp assembly is rotationally fixed to the beam element about the axis of the beam element via at least one pin that extends within the second main housing and within an axially extending alignment groove of the beam element.

32. The external fixation system of claim 29, wherein the second clamp assembly comprises a second bearing screw with a second head portion positioned within a second slot of the second main housing.

33. The external fixation system of claim 32, wherein the second slot of the second main housing extends about an axis of the central bore of the second main housing that is perpendicular to the axis of the beam element.

34. The external fixation system of claim 32, wherein the second clamp assembly further comprises a second saddle member in abutment with a second portion of the outer surface of the second main housing.

35. The external fixation system of claim 34, wherein the second portion of the outer surface of the second main housing extends partially about an axis of the central bore of the second main housing that is perpendicular to the axis of the beam element.

36. The external fixation system of claim 34, wherein the second clamp assembly further comprises a second clamp base member in abutment with the second saddle member, and a second clamp top member positioned on an opposing side the second clamp base member than the second saddle member, and wherein the second clamp assembly is configured to clamp to the at least one second fixation member between the second clamp top member and the second clamp base member.

37. The external fixation system of claim 36, wherein mating surfaces of the clamp base member and the saddle member include a friction increasing profile.

38. The external fixation system of claim 34, wherein the second bearing screw extends through the second saddle member, the second clamp base member and the second clamp top member such that a threaded portion extends past the second clamp top member, and wherein the second clamp assembly further comprises a second nut threadably engaged with the threaded portion of the second bearing screw.

39. The external fixation system of claim 38, wherein translation of the second nut along the second bearing screw towards the head portion effectuates a compressive force to the at least one second fixation member when positioned between the second clamp top member and the second clamp base member.

40. The external fixation system of claim 38, wherein translation of the second nut along the second bearing screw towards the head portion effectuates a compressive force to the second main housing between the head portion of the second bearing screw and the second saddle member to rotationally fix the second clamp assembly about the axis of the central bore.

41. The external fixation system of claim 38, wherein translation of the second nut along the second bearing screw towards the head portion effectuates a compressive force between the second saddle member and the second clamp base member to rotationally fix the second clamp base member and the second clamp top member about the second bearing screw.

42. The external fixation system of claim 29, further comprising a clamp guide positioned within the central bore of the second main housing, the clamp guide including a narrowing internally threaded aperture.

43. The external fixation system of claim 42, further comprising a clamp screw including a through aperture and an axially extending slot, wherein the clamp screw is configured to threadably engage within the narrowing internally threaded aperture of the clamp guide.

44. The external fixation system of claim 43, wherein the through aperture of the clamp screw is configured to accept a third fixation member therethrough, and wherein translation of the clamp screw within the narrowing aperture of the clamp guide effectuates a compressive force to the through aperture of the clamp screw to fix a third fixation member positioned therein to the at least one end fixation clamp assembly.

45. The external fixation system of claim 1, wherein the threads of the driving member directly engage the threaded track portion in the engaged state of the driving member, and wherein the threads of the driving member are spaced from the threaded track portion in the disengaged state of the driving member.

\* \* \* \* \*